United States Patent [19]

Nelson

[11] 4,028,419

[45] June 7, 1977

[54] 2-DECARBOXY-2-HYDROXYMETHYL-CIS-4,5-DIDEHYDRO-PGE$_1$ COMPOUNDS

[75] Inventor: Norman A. Nelson, Galesburg, Mich.

[73] Assignee: The Upjoin Company, Kalamazoo, Mich.

[22] Filed: Jan. 8, 1976

[21] Appl. No.: 647,363

[52] U.S. Cl. .................. 260/586 R; 260/343.2 R; 260/343.3 R; 260/345.1; 260/345.2; 260/346.1 R; 260/346.2 R; 260/473 R; 260/473 G; 260/488 R; 260/488 CD; 260/590 C; 260/599; 260/600 R; 260/613 R; 260/617 R; 260/618 R; 260/618 D; 260/619 D; 260/619 F; 424/305; 424/308; 424/331; 424/343

[51] Int. Cl.² .................. C07C 49/46; C07C 49/80; C07C 49/82

[58] Field of Search .............................. 260/586 R

[56] References Cited

UNITED STATES PATENTS 3,810,943    5/1974    Jones et al. ..................... 260/586 R
3,933,892    1/1976    Chadra et al. ................. 260/586 R

OTHER PUBLICATIONS

Pike "J. Org. Chem.," vol. 34, p. 3552 (1969).
Crabbe et al. "Intra Science Chem. Reports," vol. 6, p. 55, (1972).

*Primary Examiner*—Norman Morgenstern
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

22 Claims, No Drawings

2-DECARBOXY-2-HYDROXYMETHYL-CIS-4,5-DIDEHYDRO-PGE₁ COMPOUNDS

BACKGROUND OF THE INVENTION

This invention provides novel compositions of matter. This invention further provides novel processes for producing these compositions of matter.

Particularly this invention provides novel analogs of some of the known prostaglandins which differ from corresponding known prostaglandins in that these prostaglandin analogs have a primary alcohol in place of the carboxyl at C-1.

The known prostaglandins include the PGE compounds, e.g. prostaglandin $E_1$ ($PGE_1$) and prostaglandin $E_2$ ($PGE_2$).

The known prostaglandins include PGF α compounds, e.g. prostaglandin $F_{1\alpha}$ ($PGF_{1\alpha}$) and prostaglandin $F_{2\alpha}$ ($PGF_{2\alpha}$).

The known prostaglandins include PGA compounds, e.g. prostaglandin $A_1$ ($PGA_1$) and prostaglandin $A_2$ ($PGA_2$).

Each of the above mentioned known prostaglandins (PG's) is a derivative of prostanioc acid which has the following structure and carbon atom numbering

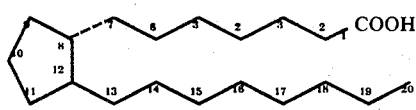

See, for example, Bergstrom et al., Pharmacol. Rev. 20, 1 (1968), and references cited therein. A systematic name for prostanoic acid is 7-[(2β-octyl)-cyclopent-1α-yl]-heptanioc acid.

$PGE_1$ has the following structure:

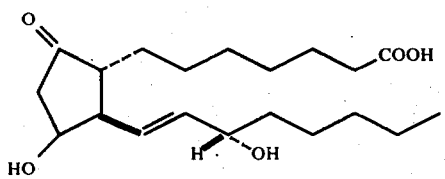

$PGE_2$ has the following structure:

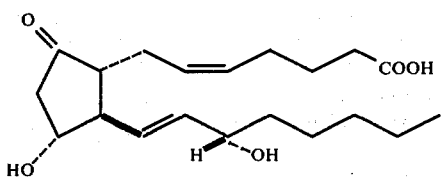

$PGF_{1\alpha}$ has the following structure:

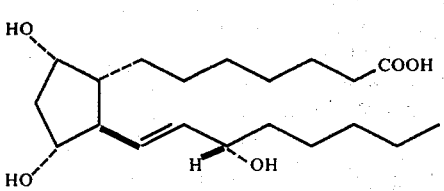

$PGF_{2\alpha}$ has the following structure:

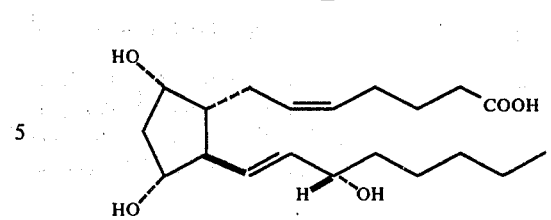

$PGA_1$ has the following structure:

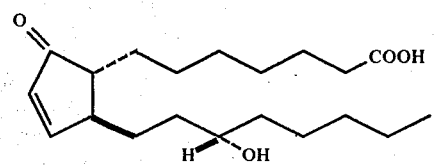

$PGA_2$ has the following structure:

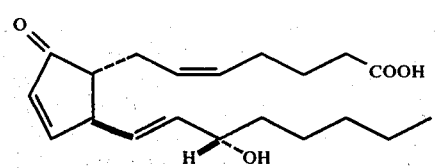

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. the use of wavy lines (∼) herein will represent attachement of substituents in either the apha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-13, C-14, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, or from carbonyl and-/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any cyclopentane derivative which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type product each represent the particular stereoisomer of the prostaglandin-type product which is of the same relative stereochemical configuration as a corresponding prostaglandin obtained from mammalian tissues, or the particular stereoisomer of the intermediate which is useful in preparing above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type compound herein, the term prostaglandin analog refers to the compound of that formula, or a mixture comprising that compound and the enantiomer thereof.

The various PG's named above, their esters, acylates and pharmacologically acceptable salts, are extremely potent in causing various biological responses. For that reason, these compounds are useful for phamcological purposes. See, for example, Bergstrom et al., Pharmacol. Rev. 20, 1 (1968) and references cited therein.

For the PGE compounds these biological responses include:

a. stimulating smooth muscle (as shown by tests, for example, on guinea pig ileum, rabbit duodenum, or gerbil colon);
b. effecting lipolytic activity (as shown by antagonism of epinephrine induced release of glycerol from isolated rat fat pads);
c. inhibiting gastric secretion and reducing undesirable gastrointestinal effects from systematic administration of prostaglandin synthetase inhibitors;
d. controlling spasm and facilitating breathing in asthmatic conditions;
e. decongesting nasal passages;
f. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);
g. affecting the reproductive organs of mammals as labor inducers, abortifacients, cervical dilators, regulators of the estrus, and regulators of the menstrual cycle; and
h. accelerating growth of epidermal cells and keratin in animals.

For the PGFα compound these biological responses include:

a. stimulating smooth muscle (as shown by tests on guinea pig ileum, rabbit duodenum, or gerbil colon);
b. inhibiting gastric secretion and reducing undesirable gastrointestinal effects from systematic administration of prostaglandin synthetase inhibitors;
c. decongesting nasal passages;
d. decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and
e. affecting the reproductive organs of mammals as labor inducers, abortifacients, cervical dilators, regulators of the estrus, and regulators of the menstrual cycle.

For the PGA compounds these biological responses include:

a. stimulating smooth muscle (as shown by tests on guinea pig ileum, rabbit duodenum, or gerbil colon);
b. inhibiting gastric secretion and reducing undesirable gastrointestinal effects from systematic administration of prostaglandin synthetase inhibitors;
c. controlling spasm and facilitating breathing in asthmatic conditions;
d. decongesting nasal passages; and
e. increasing kidney blood flow.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds, for example, are useful in place of or in combination with less than usual amounts of these known smooth muscle stimulators, for example, to relieve the symptons of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient of animal.

As mentioned above, the PGE compounds are potent antagonists of epinephrine-induced mobilization of free fatty acids. For this reason, this compound is useful in experimental medicine for both in vitro and in vivo stuides in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the antiinflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13, 14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally. Further, the prostaglandin can be conveniently administered orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g. orally in the form of tablets, capsules, or liquids; rectally in the form of suppositories; parenterally, subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et a., U.S. Pat. No. 3,644,638.

The prostaglandins so cited above as useful in mammals, including man, as nasal decongestants are used for this purpose, in a dose range of about 10 μg. to about 10 mg. per ml. of a pharmacologically suitable liquid vehicle or as an aerosol spray, both for topical application.

The protaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being perserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donar animal, to the perfused body portion, attached or detached, to the recipient, or to two or all of those at a total steady state dose of about 0.001 to 10 mg. per liter or circulating fluid. It is especially useful to use these compounds in laboratory animals, e.g., cats, dogs, rabbits, monkeys, and rats, for these purposes in order to develope new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the terms menstruating female mammals is meant animals which are mature enough to menstruate, but not so old that regular menstruation has ceased. For that purpose the prostagladin is adminstered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mamalian gestation period.

These compounds are further useful in causing cervical dilation in pregnant an nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient of animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution contaning 1 to 500 μg. per mg. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazone, furazolium chloride, and nitrofurazone, and with corticoid steriods, for example, hydrocortisone, prednisolone, methylprednisolone, and fluprednisolone, each of those being used in the combination at the usual concentration suitable for its use alone.

Several 2-decarboxy-2-hydroxymethyl prostaglandin analogs are known in the art. See, Pike, J. E., et al., Journal of Organic Chemistry 34:3552 (1969) for disclosure of 2-decarboxy-2-hydroxymethyl-$PGE_1$. See also Crabbe, et al., Intra-Science Chemical Report 6:55 (1972) which discloses 2-decarboxy-2-hydroxymethyl-$PGE_2$ and $PGF_2\alpha$. See also Fried, J. et al., Annals of the New York Academy of Sciences 180:38 (1971) which discloses 2-decarboxy-2-hydroxymethyl-13,14-didehydro-(15RS)-$PGF_{1\alpha}$. Finally, see Pike, et al., Nobel Symposium 2:161 (1967) which discloses 2-decarboxy-2-hydroxymethyl-$PGF_{1\alpha}$.

Further, the following publications disclose 2-decarboxy-2-hydroxymethyl prostaglandin analogs: German Offenlengungsschrift 2,437,388 (Derwent Farmdoc CPl No. 43108W); Belgian Pat. No. 817513 (Derwent Farmdoc CPl No. 07432W); German Offenlegungsschrift 2,404,653 (Derwent Farmdoc CPl No. 57272V); German Offenlegungsschrift 2,360,893 (Derwent Farmdoc CPl No. 45723V); Netherlands Pat. No. 7,206,361 (Derwent Farmdoc CPl No. 76383T); Netherlands Pat. No. 7,209,817 (Derwent Farmdoc CPl No. 05789U); Netherlands Pat. No. 7,209,738 (Derwent Farmdoc CPl No. 05786U); Netherlands Pat. No. 7,306,030 (Derwent Farmdoc CPl No. 71295U);Netherlands Pat. No. 7,313,322 (Derwent Farmdoc CPl No. 28414V); Belgian Pat. No. 815,372 (Derwent Farmdoc CPl No. 84521V); and Belgian Pat. No. 815,742 (Derwent Farmdoc CPl No. 81796V). Finally, see U.S. Pat. No. 3,852,377 which describes PGF-tetraols, and Belgian Pat. No. 722,031 (Derwent Farmdoc CPl No. 37,298).

SUMMARY OF THE INVENTION

This invention provides novel prostaglandin analogs, esters of these analogs, and pharmacologically acceptable salts of these analogs.

This invention further provides lower alkanoates of these analogs.

This invention further provides novel processes for preparing these analogs.

In particular, this invention comprises:
a. a prostaglandin analog of the formula

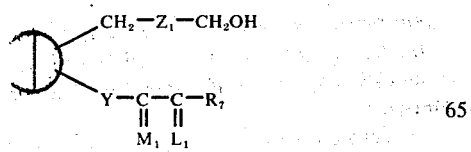

wherein is

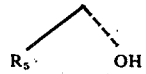

wherein
$R_8$ is hydrogen or hydroxy;
wherein Y is trans—CH=CH—;
wherein $M_1$ is

or

wherein $R_5$ is hydrogen or methyl;
wherein $L_1$ is

-continued

or a mixture of

and

wherein $R_3$ and $R_4$ are hydrogen, methyl or fluoro, being the same or different, with the proviso that one of $R_3$ and $R_4$ is methyl only when the other is hydrogen or methyl;

wherein $Z_1$ is cis—CH=CH—CH$_2$—(CH$_2$)$_g$—CF$_2$—, cis—CH$_2$—CH=CH—(CH$_2$)$_g$—CH$_2$—, —(CH$_2$)$_3$—(CH$_2$)$_g$—CF$_2$—, —CH$_2$—O—(CH$_2$)$_g$—CH$_2$—,

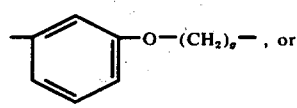, or

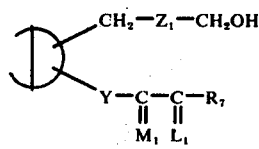, wherein g is one, 2, or 3;
wherein $R_7$ is —(CH$_2$)$_m$—CH$_3$, wherein m is one to 5, inclusive;

b. a prostaglandin analog of the formula

wherein

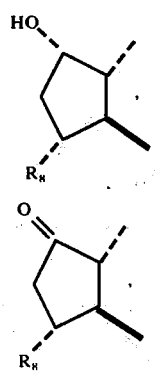 is

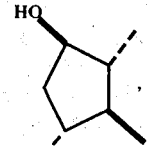

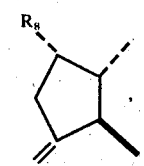

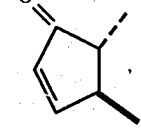, or

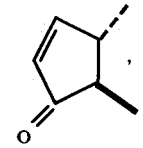

wherein $R_8$ is hydrogen or hydroxy;
wherein Y is trans—CH=CH—;
wherein $M_1$ is

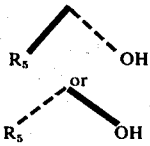

or

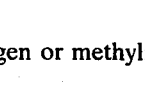, or
wherein $R_5$ is hydrogen or methyl;
wherein $L_1$ is

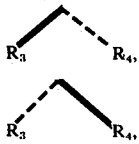

or a mixture of

and

wherein $R_3$ and $R_4$ are hydrogen, methyl, or fluoro, being the same or different, with the proviso that one of $R_3$ and $R_4$ is methyl only when the other is hydrogen or methyl;
wherein $Z_1$ is cis—CH=CH—CH$_2$—(CH$_2$)$_g$—CH$_2$—, cis—CH$_2$—CH=CH—(CH$_2$)$_g$—CH$_2$—, —(CH$_2$)$_3$—(CH$_2$)$_g$—CF$_2$—, —CH$_2$—O—(CH$_2$)$_g$—CH$_2$—,

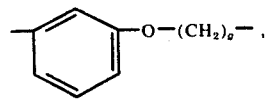

or

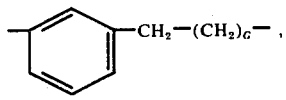

wherein g is one, 2, or 3;
wherein $R_7$ is

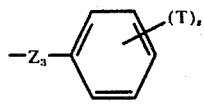

wherein $Z_3$ is methylene or oxa, $s$ is zero, one, 2, or 3 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl; with the further proviso that $Z_3$ is oxa only when $R_3$ and $R_4$ are hydrogen or methyl, being the same or different; or c. a prostaglandin analog of the formula

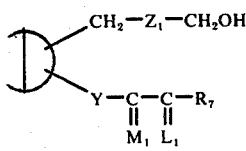

wherein

is

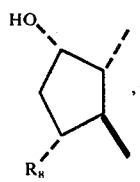

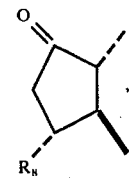

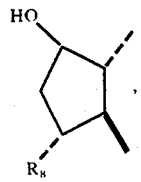

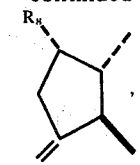

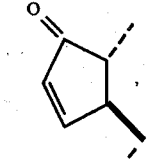, or

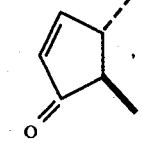

wherein $R_8$ is hydrogen or hydroxy;
wherein Y is trans—CH=CH—;
wherein $M_1$ is

or

wherein $R_5$ is hydrogen or methyl;
wherein $L_1$ is

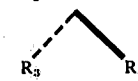

or a mixture of

and

wherein $R_3$ and $R_4$ are hydrogen, methyl, or fluoro, being the same or different, with the proviso that one of $R_3$ and $R_4$ is methyl only when the other is hydrogen or methyl; and
wherein $Z_1$ is cis—CH=CH—$CH_2(CH_2)_g$—$CH_2$— or —$(CH_2)_3$—$(CH_2)_g$—$CH_2$—, wherein g is one, 2, or 3;
wherein $R_7$ is —$(CH_2)_m$—$CH_3$, wherein m is one to 5, inclusive;
with the proviso that at least one of $R_3$, $R_4$, and $R_5$ is methyl or at least one of $R_3$ and $R_4$ is fluoro.

Within the scope of the novel prostaglandin analogs of this invention, there are represented above:
 a. 2-decarboxy-2-hydroxymethyl-PGE-type compounds when the cyclopentane moiety is:

15

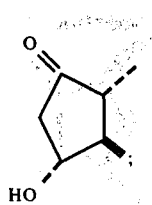

b. 2-decarboxy-2-hydroxymethyl-PGF -type compounds when the cyclopentane moiety is:

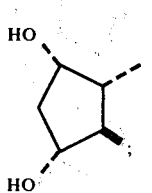

c. 2-decarboxy-2-hydroxymethyl-PGD-type compounds when the cyclopentane moiety is:

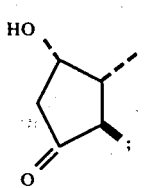

d. 2-decarboxy-2-hydroxymethyl-9-deoxy-PGD-type compounds when the cyclopentane moiety is:

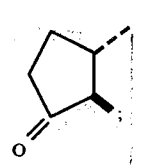

e. 2-decarboxy-2-hydroxymethyl-9-deoxy-9,10-didehydro-PGD-type compounds when the cyclopentane moiety is:

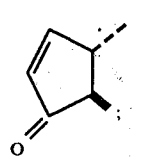

f. 2-decarboxy-2-hydroxymethyl-11-deoxy-PGE-type compounds when the cyclopentane moiety is:

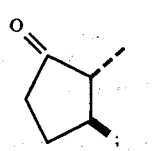

g. 2-decarboxy-2-hydroxymethyl-11-deoxy-PGF -type compounds when the cyclopentane moiety is:

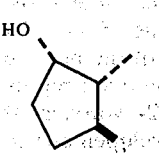

and h. 2-decarboxy-2-hydroxymethyl-PGA-type compounds when the cyclopentane moiety is:

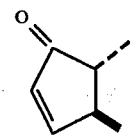

Those prostaglandin analogs herein wherein $Z_1$ is cis—CH=CH—CH$_2$—(CH$_2$)$_g$—C(R$_2$)$_2$— wherein $R_2$ is hydrogen or fluoro, are named as "PG$_2$" compounds. When $R_2$ is fluoro these compounds are further characterized as "2,2-difluoro" PG-type compounds. When $g$ is 2 or 3 the prostaglandin analogs so described are "2a-homo" or "2a,2b-dihomo" compounds, since in this event the carboxy terminated side chain containsl 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —(CH$_2$)$_3$—(CH$_2$)$_g$—C(R$_2$)$_2$—, wherein $g$ is as defined above, the compounds so described are "PG$_1$" compounds. When $g$ is 2 or 3, the "2a-homo" and "2a,2b-dihomo" compounds are described is discussed in the preceeding paragraph. Also, "2,2-difluoro" compounds are described when $R_2$ is fluoro.

When $Z_1$ is —CH$_2$—O—(CH$_2$)$_g$—CH$_2$— the compounds so described are named as "5-oxa-PG$_1$" compounds. When $g$ is 2 or 3, the compounds so described are "2a-homo" or "2a,2b-dihomo" compounds, respectively, as discussed above.

When $Z_1$ is cis—CH$_2$—CH=CH—(CH$_2$)$_g$—CH$_2$—, wherein $g$ is as defined above, the compounds so described are cis-4,5-didehydro-PG$_1$" compounds. When $g$ is 2 or 3, the compounds so described are further characterized as "2a-homo" or "2a,2b-dihomo" compounds, respectively, as discussed above.

When $R_7$ is —(CH$_2$)$_m$—CH$_3$, wherein $m$ is as defined above, the compounds so described are named as "19,20-dinor", "20-nor", "20-methyl", or "20- ethyl compounds when $m$ is one, 2, 4, or 5, respectively.

When $R_7$ is

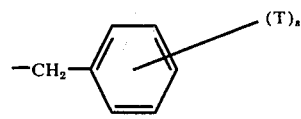

wheren $T$ and $s$ are as defined above, the compounds so described are named as "17-phenyl-18,19,20-trinor" compounds, when $s$ is O. When $s$ is one, 2, or 3, the corresponding compounds are named as "17-(substituted phenyl)18,19,20-trinor" compounds.

When $R_7$ is

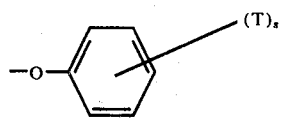

wherein T and s are as defined above, and neither R₃ nor R₄ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds: When one and only one of R₃ and R₄ is methyl or both R₃ and R₄ are methyl, then the corresponding compounds wherein R₇ is as defined in this paragraph as named as "16-phenoxy or 16-(substituted phenoxy)-18,19,20-trinor"compounds or "16-methyl-16-phenoxy or 16-(substituted phenoxy)-18,19,20-trinor" compounds, respectively.

When at least one of R₃ and R₄ is not hydrogen then (except for the 16-phenoxy compounds discussed above) there are described the "16-methyl" (one and only one of R₃ and R₄ is methyl), "16,16-dimethyl" (R₃ and R₄ are both methyl), "16-fluoro" (one and only one of R₃ and R₄ is fluoro), "1,6,16-difluoro" (R₃ and R₄ are fluoro) compounds. For those compounds wherein R₃ and R₄ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When R₅ is methyl, the compounds so described are named as "15-methyl" compounds.

For a general description of the nomenclature employed herein, see N. A. Nelson, J. of Med. Chem. 17, 911 (1974).

PG-type compounds as drawn herein which have an hydroxy at C-15 in the beta configuration are of the opposite relative stereochemical configuration at C-15 as that of PGE₁, and are therefore named as "15-epi" compounds. When the alpha hydroxy configuration is present, no special designation of this stereochemistry is provided in naming the compound.

Examples of

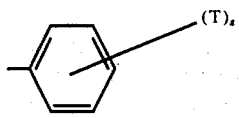

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)-ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, o-, m-, or p-trifluoromethyl)-phenyl, (o-, m-, or p-)methoxyphenyl (o-, m-, or p-)ethoxyphenyl, (4- or 5-)chloro-2-methoxyphenyl, and 2,4-dichloro(5- or 6-)methylphenyl.

The novel prostaglandin analogs of this invention correspond to the prostaglandins described above, in that the novel prostaglandin analogs exhibit prostaglandin-like activity.

Specifically the PGE- and 11-deoxy-PGE-type compounds of this invention correspond to the PGE compounds described above, in that these novel PGE- and 11-deoxy-PGE-type compounds are useful for each of the above-described purposes for which the PGE compounds are used, and are used in the same manner as the PGE compounds, as described above.

The PGF$_\alpha$ - and 11-deoxy-PGF$_\alpha$ -type compounds of this invention correspond to the PGF$_\alpha$ compounds described above, in that these novel PGF$_\alpha$ - and 11-deoxy-PFG$_\alpha$ -type compounds are useful for each of the above-described purposes for which the PGF$_\alpha$ compounds are used, and are used in the same manner as the PGF$_\alpha$ compounds, as described above.

The PGD-, 9-deoxy-PGD-, and 9,10-didehydro-9-deoxy-PGD-type compounds of this invention correspond to the PGE or PGF$_\alpha$ compounds described above, in that these novel PGD-, 9-deoxy-PGE-, or 9-deoxy-9,10-didehydro-PGD-type compounds are useful for each of the above-described purposes for which either the PGE or PGF$_\alpha$ compounds are used, and are used in the same manner as the PGE or PFG$_\alpha$ compounds, as described above.

The PGA-type compounds of this invention correspond to the PGA compounds described above, in that these novel PGA-type compounds are useful for each of the above described purposes for which the PGA compounds are used, and are used in the same manner as the PGA compounds, as described above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, shorter, or smaller doses, and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For subcutaneous or intramuscular injection, sterile solutions or suspension of a compound in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The chemical structure of the novel 11-deoxy-2-decarboxy-2-hydroxymethyl-PGE-type compounds of this invention renders them less sensitive to dehydration and rearrangement than the corresponding prostaglandins, and these compounds accordingly exhibit a surprising and unexpected stability and duration of shelf life.

To obtain the optimum combination of biological response specificity, potency, and duration of activity, certain compounds within the scope of this invention are preferred.

It is preferred that the carboxy-terminated side chain contain either 7 or 9 carbon (or carbon and oxygen) atoms, especially preferred that it contain 7, i.e., the natural chain length of the prostaglandins. Further when $R_7$ is $—(CH_2)_m—CH_3$, it is preferred that $m$ be 3. For those compounds wherein $R_7$ is -O-⟨phenyl⟩-(T)$_s$ or -CH$_2$-⟨phenyl⟩-(T)$_s$ it is preferred that $s$ be zero or one and T be chloro, fluoro, or trifluoromethyl.

For those compounds wherein at least one of $R_3$ and $R_4$ is methyl or fluoro, it is preferred that $R_5$ be hydrogen. For those compounds wherein $R_5$ is methyl, it is preferred that $R_3$ and $R_4$ both be hydrogen. For those compounds wherein $R_7$ is -O-⟨phenyl⟩-(T)$_s$ or -CH$_2$-⟨phenyl⟩-(T)$_s$ 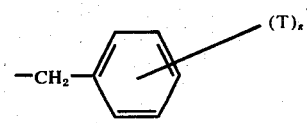

it is preferred $R_3$ and $R_4$ by hydrogen.

It is further preferred that the 15-hydroxy not be of the 15-epi configuration, i.e., that the hydroxy be in the alpha configuration when the formulas of the novel PG analogs are as shown herein.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences described preferred compounds within the scope of the each formula of a prostaglandin analog provided in the Tables hereinafter.

In another aspect of the interpretation the preferences herein, the various prostaglandin cyclopentane ring structures as employed herein are each representative of a particular "parent structure" which is useful in naming and categorizing the novel prostaglandin analogs disclosed herein. Further, where a formula depicts a genus of PG analogs disclosed herein evidencing a single cyclopentane ring structure, then each corresponding genus of PG analogs evidencing one of the remaining cyclopentane ring structures cited herein for novel prostaglandin analogs is intended to represent an equally preferred genus of compounds. Thus, for example, for each genus of PGF$_\alpha$ -type products depicted by a formula herein the corresponding genera of PGD-, PGE-, and 11-deoxy-PGF$_\alpha$ -type products are equally preferred embodiments of the invention as the genus of PGF$_\alpha$ -type products.

Finally where subgeneric grouping of PG analogs of any cyclopentane ring structure are described herein, then the corresponding subgeneric groupings of PG analogs of each of the remaining cyclopentane ring structures are intended to represent equally preferred embodiments of the present invention.

The Charts herein describe methods whereby the novel prostaglandin analogs of this invention are prepared.

With respect to the Charts, $R_2$, $R_7$, $R_8$, $M_1$, $L_1$, Y, $Z_1$, $Z_3$, and g are as defined above.

is as defined above The symbol "n" is one or two, $M_{5l}$ is

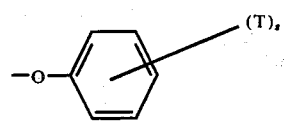

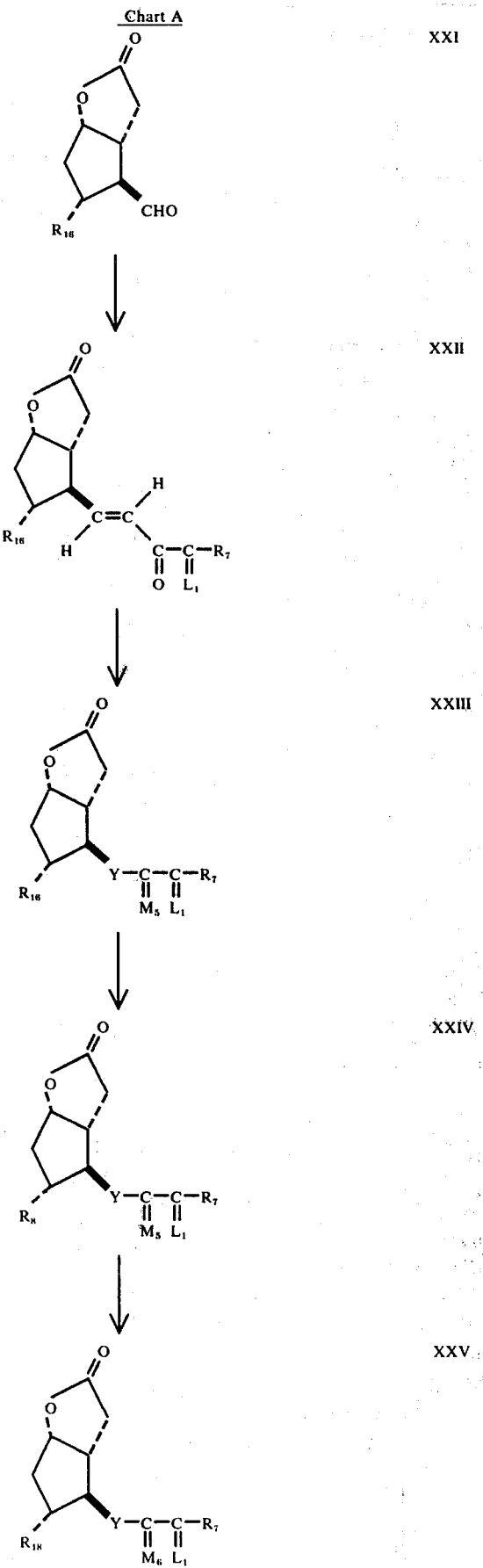

-continued
Chart A
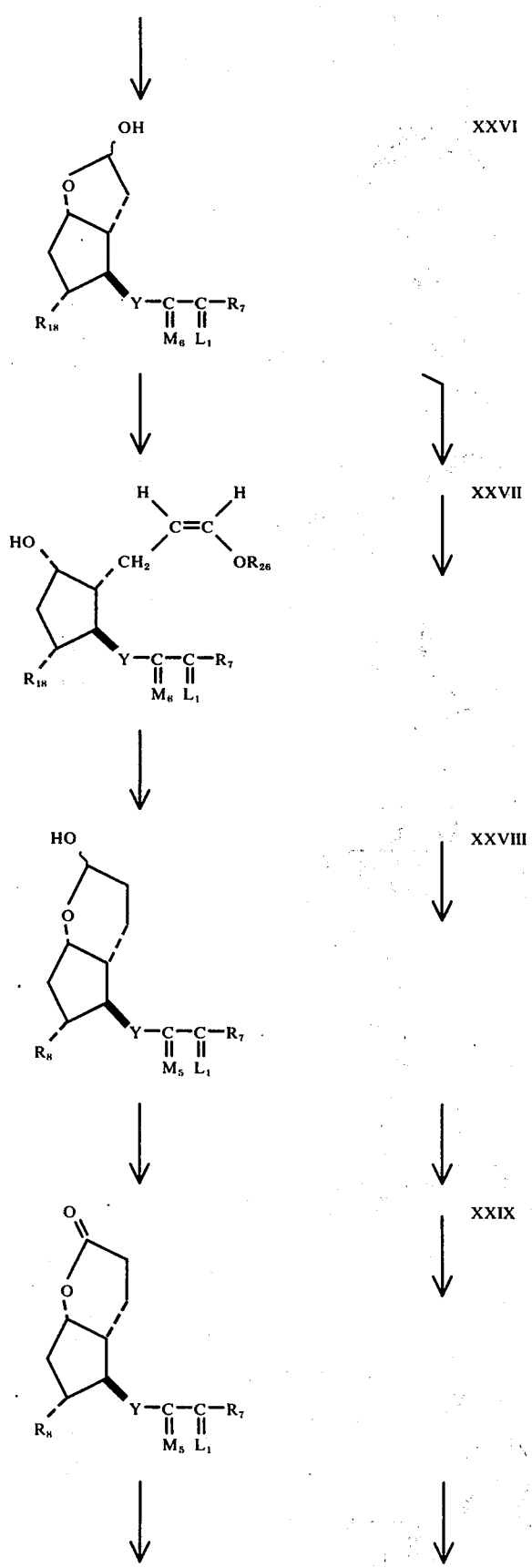
XXVI
XXVII
XXVIII
XXIX

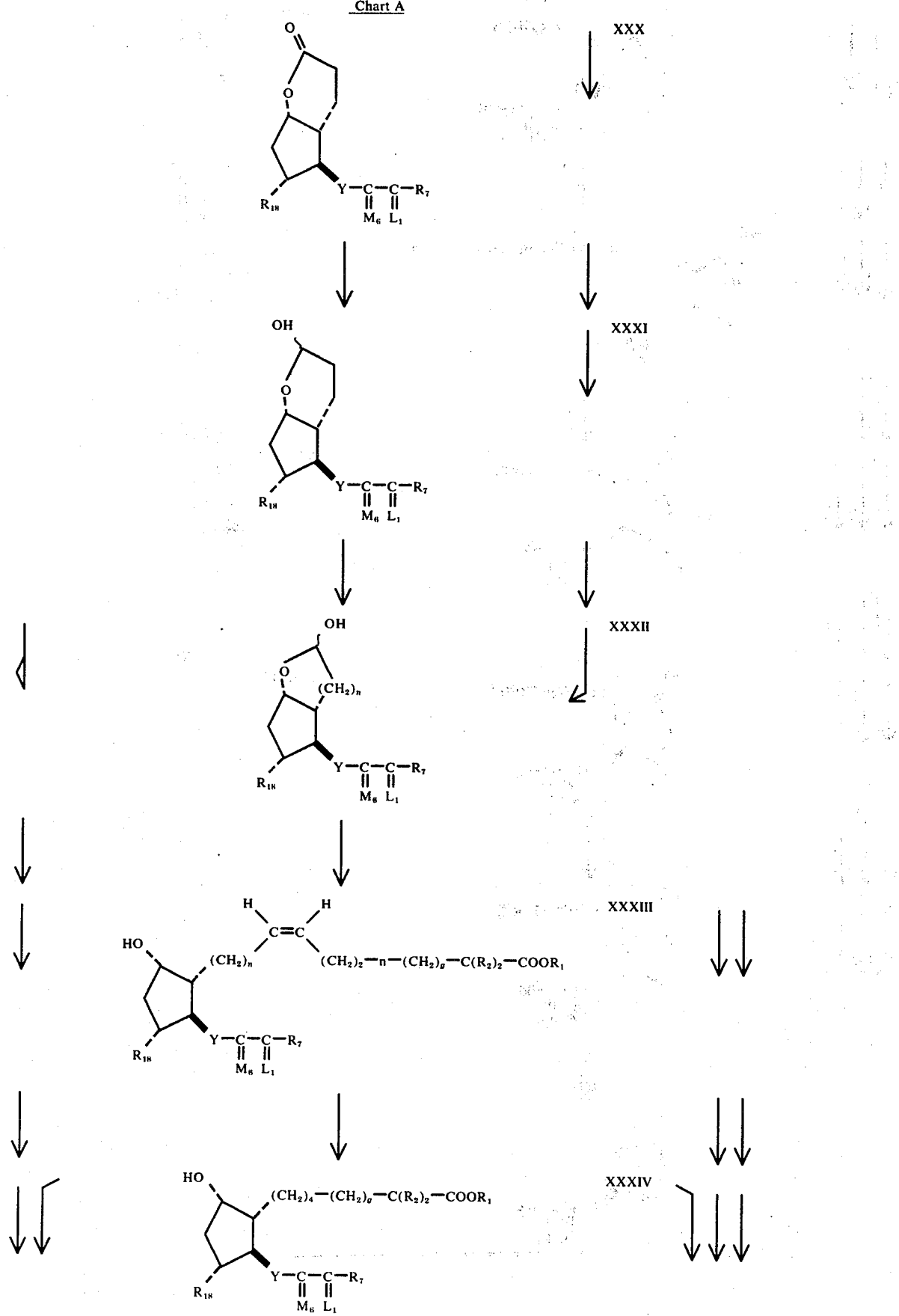

-continued
Chart A
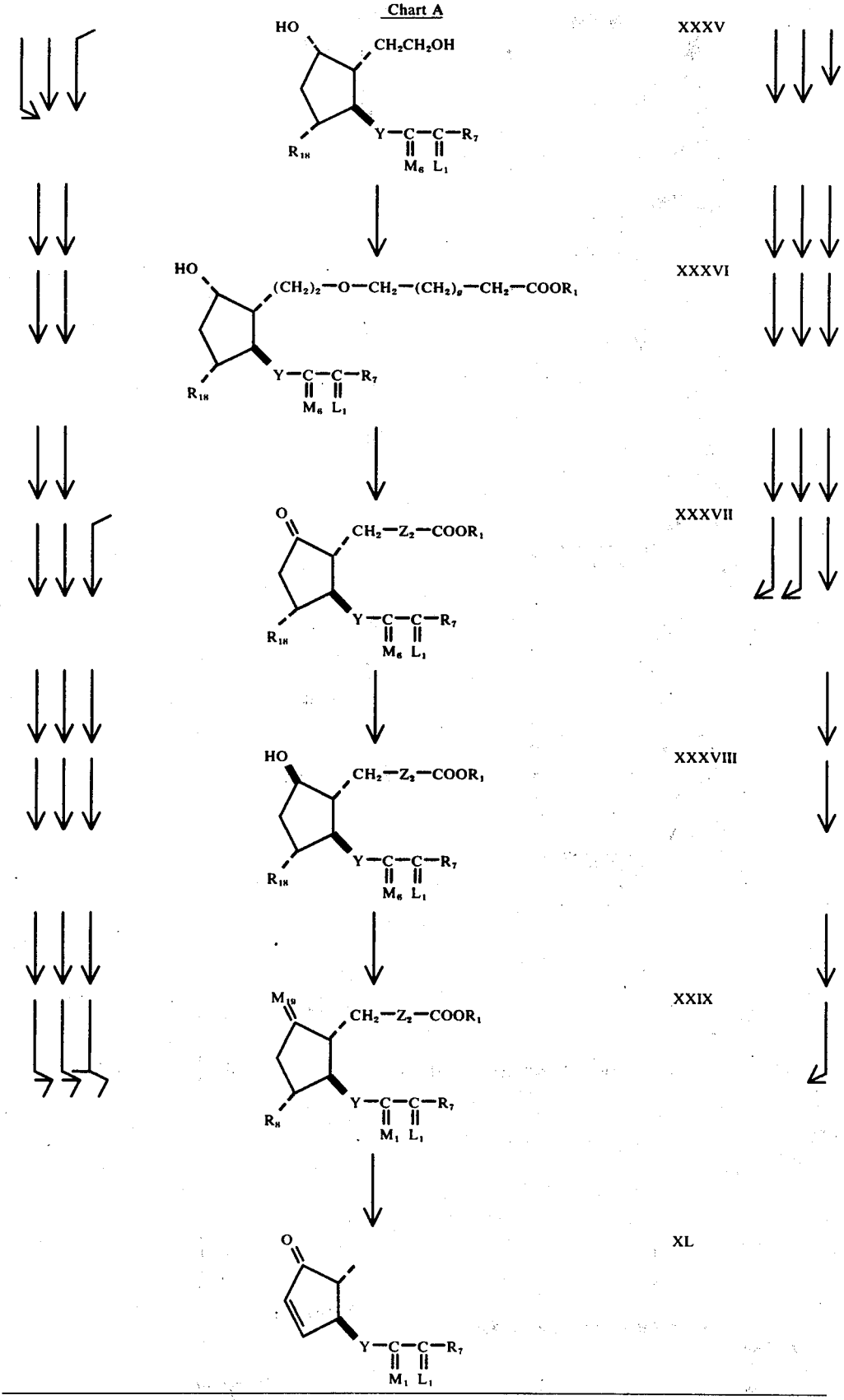

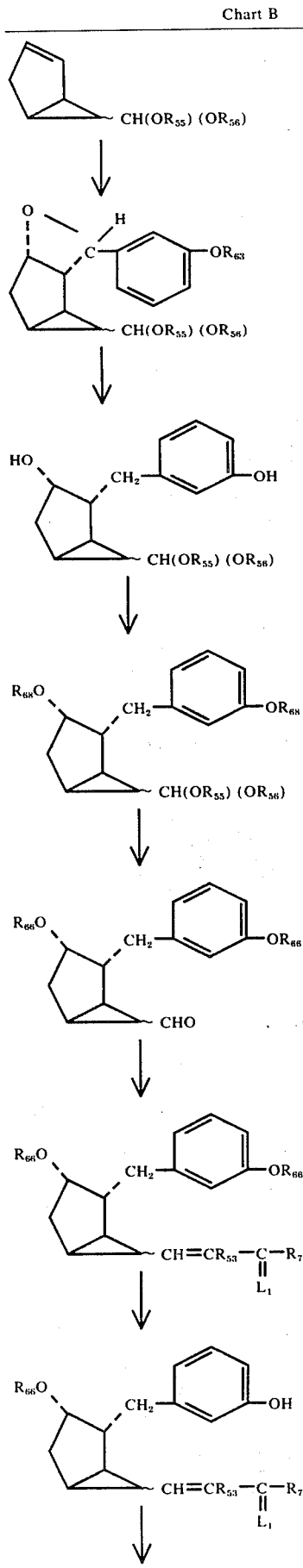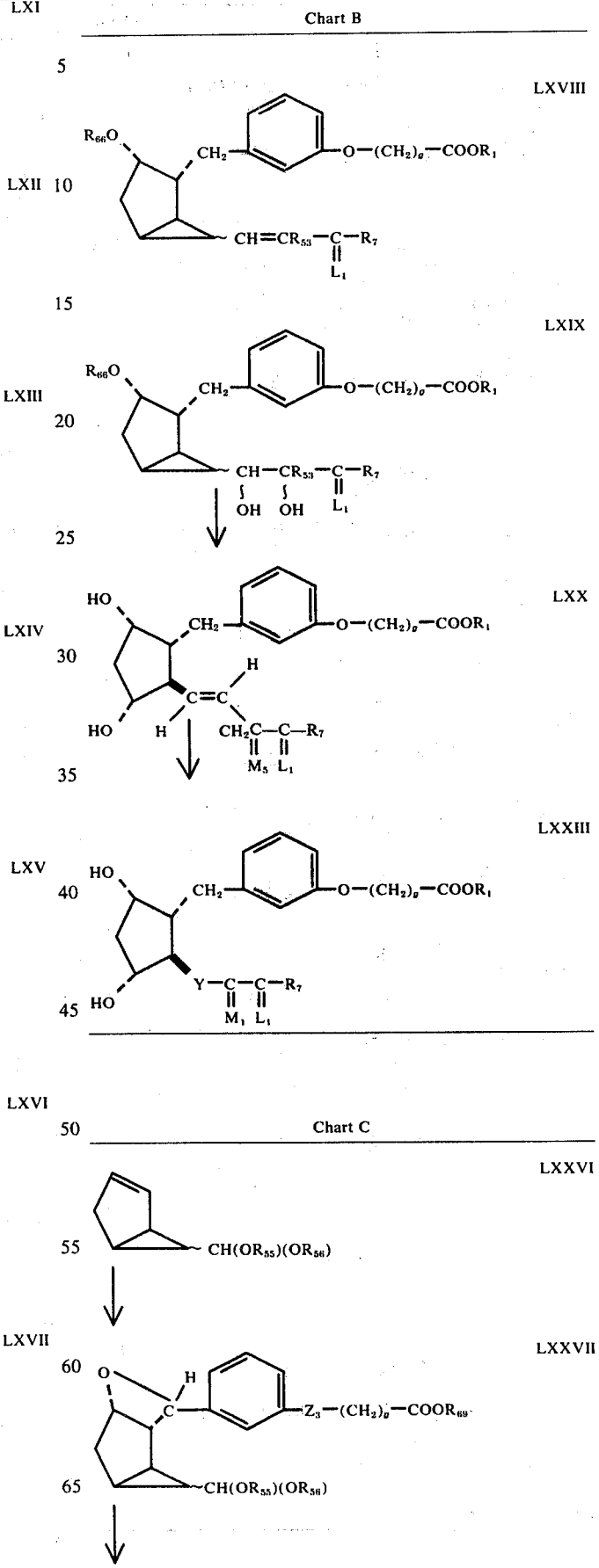

-continued
Chart C
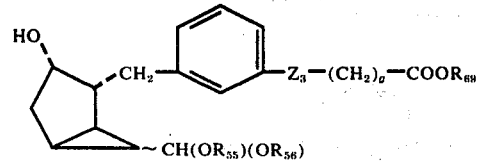
LXXVIII
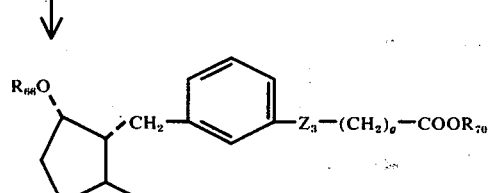
LXXIX
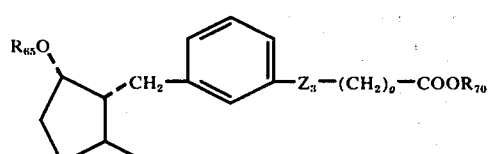
LXXX
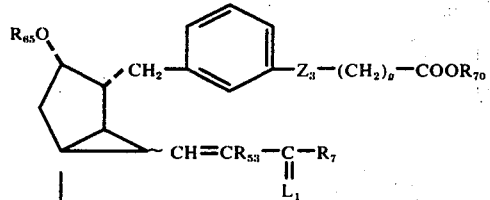
LXXXI
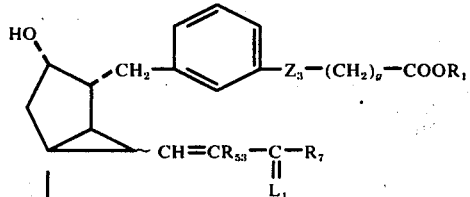
LXXXII
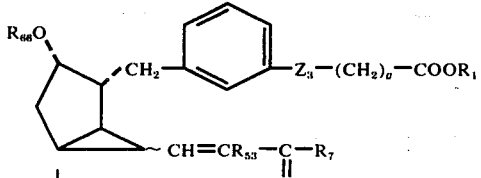
LXXXIII
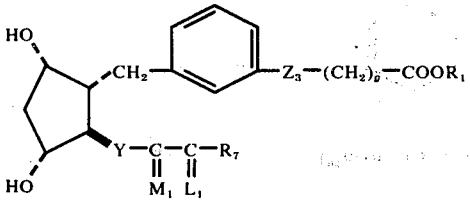
LXXXIV
Chart D
XCI
XCII
XCIII
XCIV
Chart E
CI
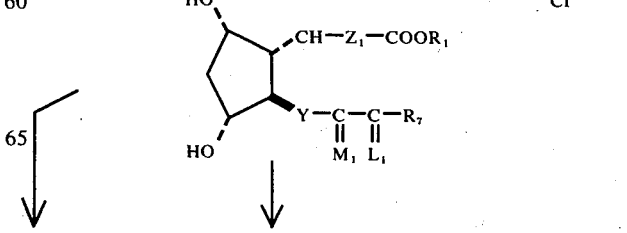

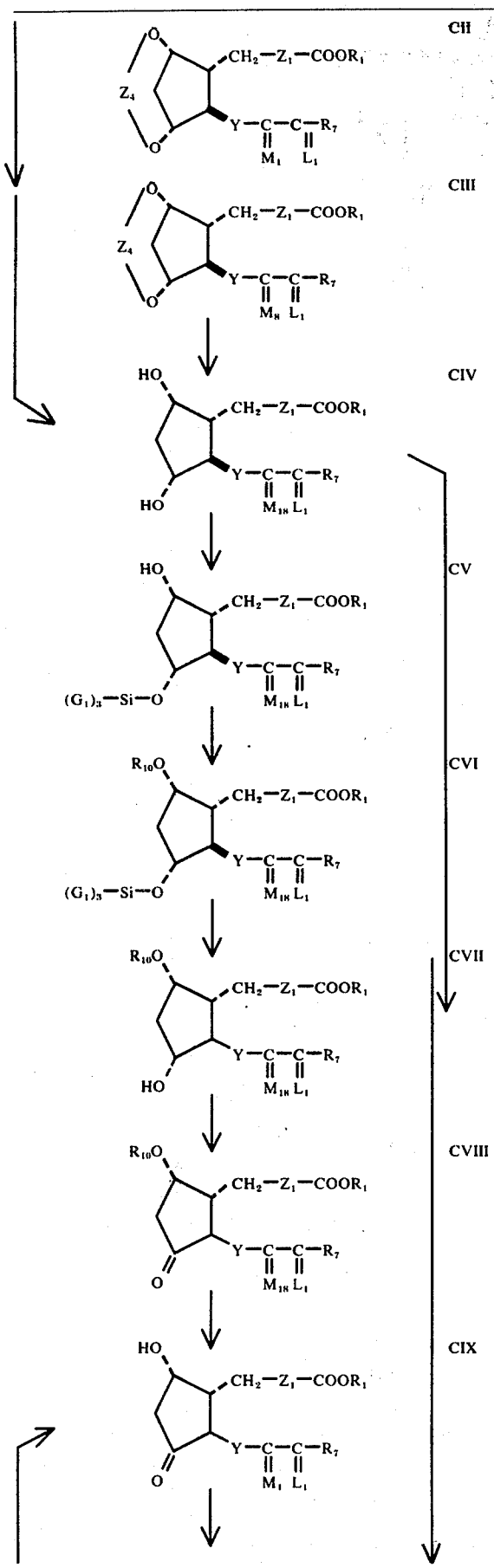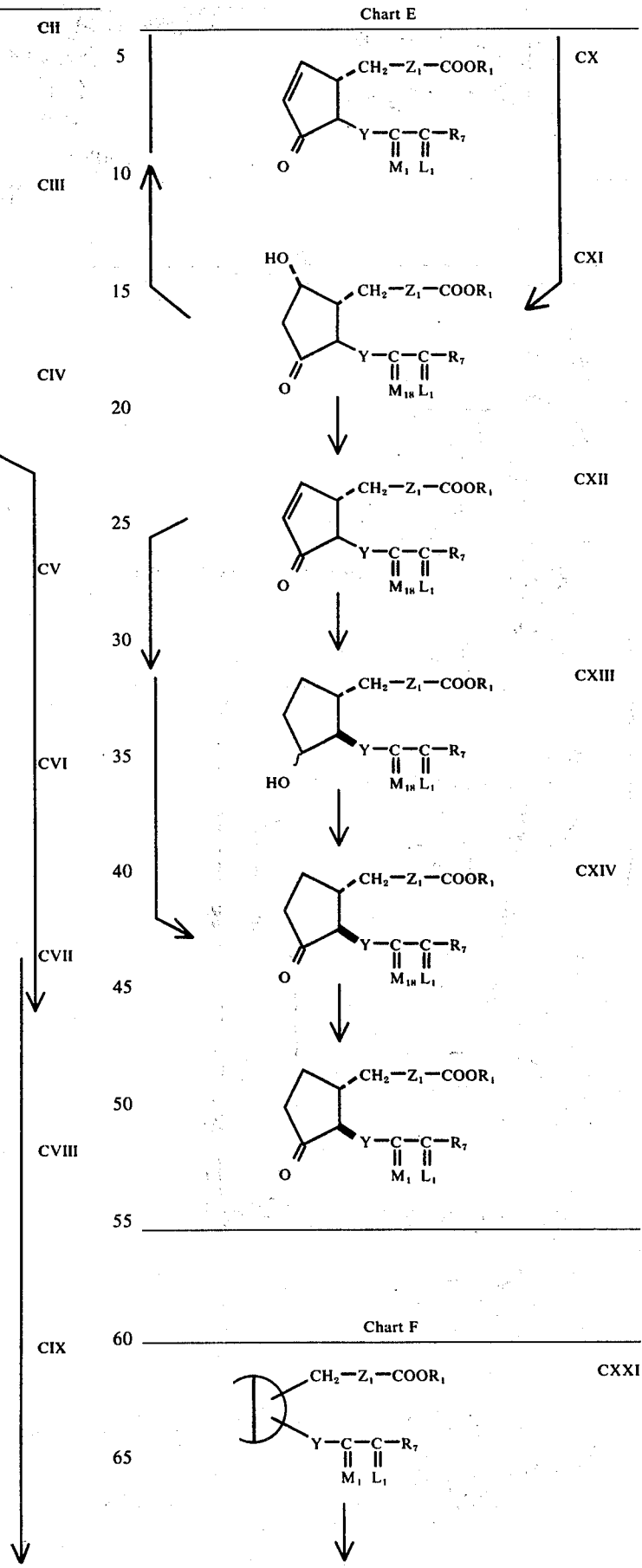

-continued
Chart F
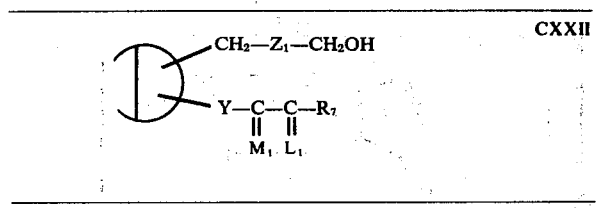
CXXII
Chart H
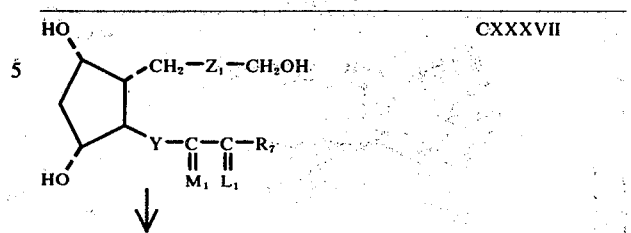
CXXXVII
Chart G
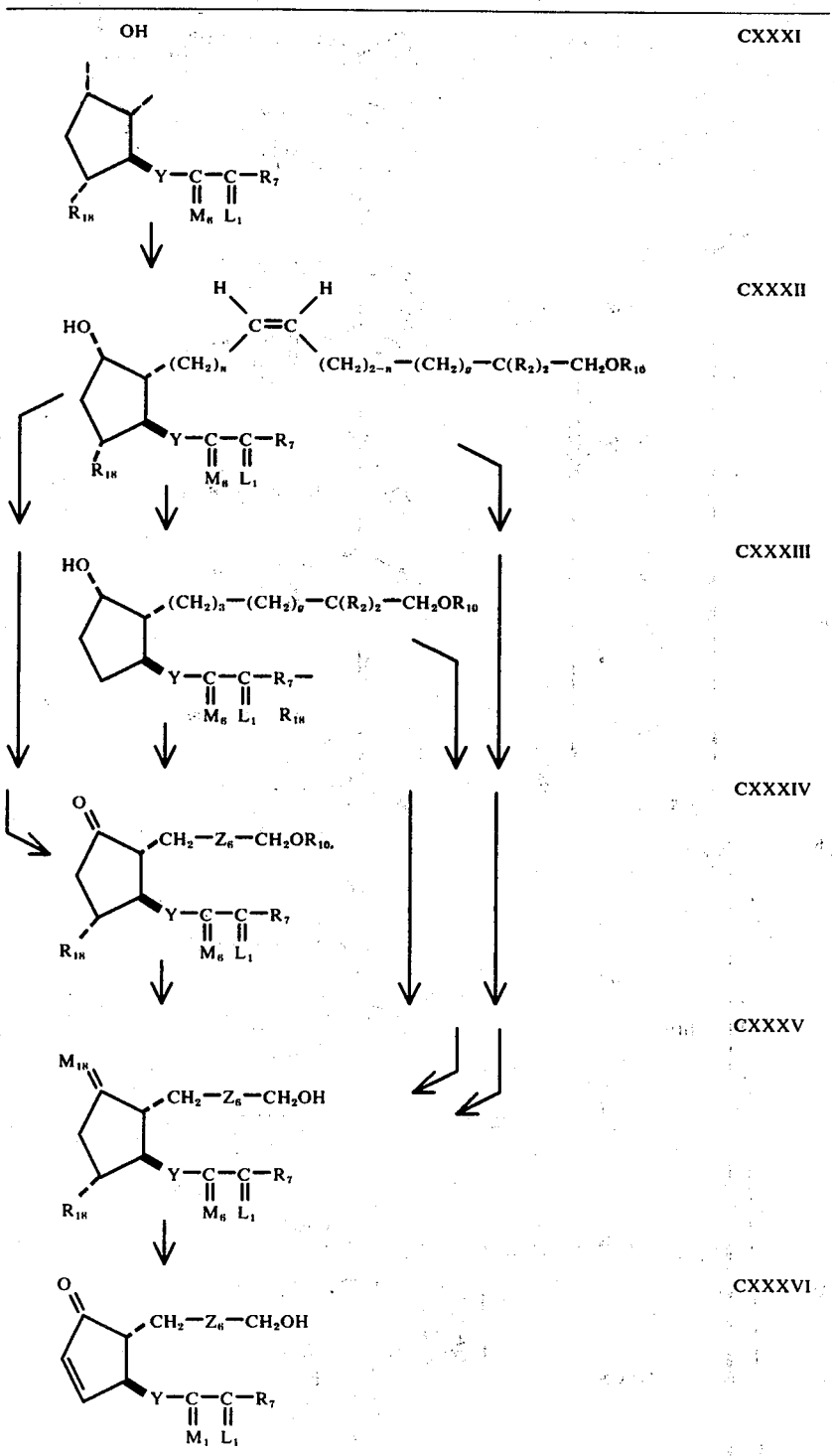
CXXXI
CXXXII
CXXXIII
CXXXIV
CXXXV
CXXXVI -continued
Chart H

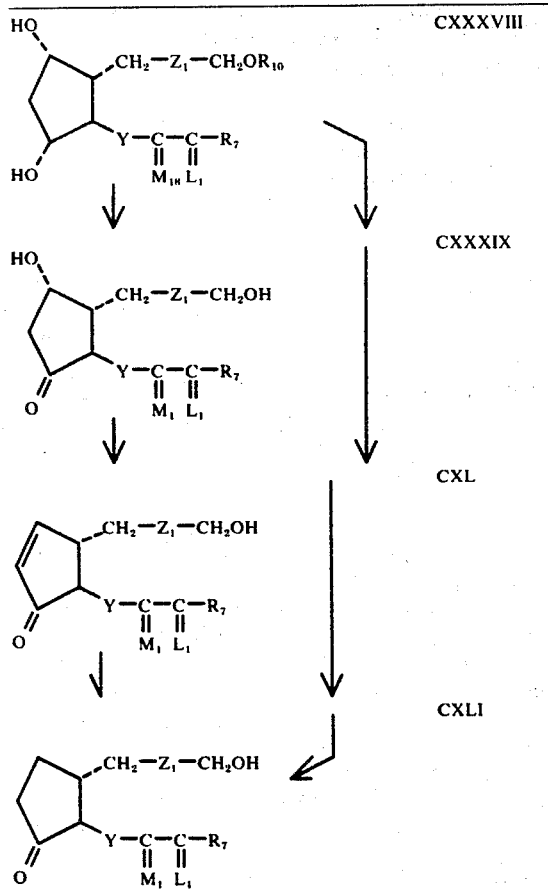

or a mixture of

and

$M_6$ is

or

or the mixture of epimers thereof wherein $R_{10}$ is a blocking group and $R_5$ is as defined above. $M_8$ is

or

wherein $R_{10}$ is a blocking group. $M_{19}$ is

or

$M_{18}$ is

or

wherein $R_{10}$ is a blocking group. $R_{16}$ is hydrogen or $-OR_9$, wherein $R_9$ is an acyl protecting group. $R_{18}$ is hydrogen or $-OR_{10}$, wherein $R_{10}$ is a blocking group. $R_{26}$ is hydrocarbyl, including alkyl, aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1methyl-3-phenylpropyl, cyclohexyl, phenyl, and p-methylphenyl.

$G_1$ is alkyl of one to 4 carbon atoms, aralkyl of 7 to 12 carbon atoms, phenyl, or phenyl substituted with one or 2 fluoro, chloro, or alkyl of one to 4 carbon atoms, with the proviso that in the $-Si-(G_1)_3$ moiety the various $G_1$'s are the same or different. Preferably one of $G_1$ is tertbutyl; and the remaining 2 are methyl.

$R_1$ is hydrogen, alkyl, cycloalkyl, aralkyl, or phenyl.

$R_9$ is an acyl protecting group. Acyl protecting groups according to $R_9$, include:

a. benzoyl;
b. benzoyl substituted with one to 5 alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;
c. benzoyl substituted with alkoxycarbonyl of 2 to 5 carbon atoms, inclusive;
d. naphthoyl;
e. naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or
f. alkanoyl of 2 to 12 carbon atoms, inclusive.

In preparing these acyl derivatives of a hydroxycontaining compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of the dehydrating agent, e.g. sulfuric acid, zinc chloride, or p-toluenesulfonic acid; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides (($R_9)_2O$), or acyl chlorides ($R_3Cl$): benzoyl; substituted benzoyl, e.g., 2-, 3-, or 4-)-methylbenzoyl, (2-, 3-, or 4-)-ethylbenzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-netrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor is reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include a. tetrahydropyranyl;
b. tetrahydrofuranyl; and
c. a group of the formula

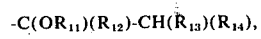

$-C(OR_{11})(R_{12})-CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c$, wherein $a$ is 3, 4, or 5, or $b$ is one, 2, or 3, and $c$ is one, 2, or 3, with the proviso that $b$ plus $c$ is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an enert solvent, e.g. dichloromethane, in the presence of an acid condensing agent such as p-toluenesulfonic acid or pyridine hydrochloride. The dihydropyran is used in large stoichoimetric excess, preferably 4 to 10 times the stoichoimetric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula

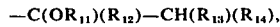

$-C(OR_{11})(R_{12})-CH(R_{13})(R_{14})$, wherein $R_{11}$, $R_{12}$, $R_{13}$, and $R_{14}$ are as defined above, the appropriate reagent is a vinyl ether, e.g. isobutyl vinyl ether or any vinyl ether of the formula

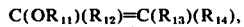

$C(OR_{11})(R_{12})=C(R_{13})(R_{14})$, wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

$R_{26}$ is hydrocarbyl, e.g. alkyl, cycloalkyl, aralkyl, and the like. Preferably $R_{26}$ is alkyl, being most preferably lower alkyl (e.g., methyl or ethyl).

$R_{51}$ is $R_{30}-SO_2$, wherein $R_{30}$ is alkyl, cycloalkyl, aralkyl, phenyl, or phenyl substituted with alkyl or halogen.

$R_{53}$ is hydrogen or methyl,.

$R_{55}$ and $R_{56}$ are aralkyl of one to 4 carbon atoms, inclusive, being the same or different, or when taken together represent a group of the formula

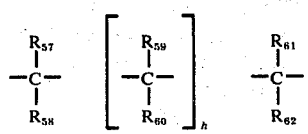

wherein $R_{57}$, $R_{58}$, $R_{59}$, $R_{60}$, $R_{61}$, and $R_{62}$ are hydrogen, alkyl of one to 4 carbon atoms, inclusive, or phenyl, being the same or different, with the proviso that not more than one of $R_{57}$, $R_{58}$, $R_{59}$, $R_{60}$, $R_{61}$, and $R_{62}$ is phenyl and that the total number of carbon atoms in $R_{57}$, $R_{58}$, $R_{59}$, $R_{60}$, $R_{61}$, and $R_{62}$ is from 2 to 10, inclusive, and $h$ is zero or one.

$R_{63}$ is carboxyacyl of the formula

wherein $R_{64}$ is hydrogen, alkyl of one to 19 carbon atoms, inclusive, or aralkyl of 7 to 12 carbon atoms, inclusive, wherein the above alkyl or aralkyl are substituted with zero to 3 fluoro, chloro, bromo, or iodo. $R_{66}$ is hydrogen or a blocking group, according to $R_{65}$. Blocking groups according to $R_{65}$ useful for the purposes of this invention include all blocking groups according to $R_{10}$, as enumerated herein, and additionally $-Si(G_1)_3$, wherein $G_1$ is alkyl of one to 4 carbon atoms, inclusive, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, inclusive. In the use of these silyl blocking groups, according to $R_{65}$, methods known in the art for the preparation of the necessary reagents and appropriate reaction conditions for replacing hydroxy hydrogens with these silyl blocking groups and subsequently hydrolyzing these silyl blocking groups, are employed. $R_{68}$ is hydrogen, carboxyacyl according to $R_{63}$, or an acyl protecting group according to $R_9$. $R_{69}$ is hydrogen or alkyl of one to 4 carbon atoms, inclusive, or silyl of the formula $-Si(G_1)_3$, wherein $G_1$ is as defined above.

The process steps of Chart A are generally known in the art using known reagents and starting materials.

With respect to Chart A the formula XXI compound is known in the art. This compound is available in either optically active or racemic form. The formula XXI compound in racemic form may be transformed into corresponding optically active compound by methods known in the art.

The formula XXII compound is prepared from the formula XXI compound by a Wittig alkylation. Reagents known in the art or prepared by methods known in the art are employed. The trans-enone lactone is obtained stereospecifically. See for reference D. H. Wadsworth, et al., Journal of Organic Chemistry 30, 680 (1965).

In the preparation of the formula XXII compound, certain phosphonates are employed in the Wittig reaction. These phosphonates are of the general formula

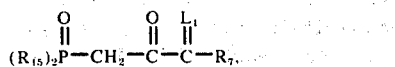

wherein $L_1$ and $R_7$ are as defined above and $R_{15}$ is alkyl of one to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula

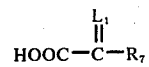

are employed in the form of their lower alkyl esters, preferably methyl or ethyl. The methyl esters for example are readily obtained by reaction of the corresponding acids with diazomethane.

For example, when $R_7$ is

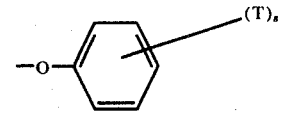

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)(trifluoromethyl)phenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichlorophenoxy-, (4- or 6 -chloro-o-tolyloxy-, phenoxy-, (o-, m-, or p-)tolyloxy, 3,5-xylyloxy-, or m-(trifluoromethyl)phenoxy-.

Finally there are available many 2-methyl- 2 -phenoxy-or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_1$ is: phenoxy-, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the $(T)_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is benzyl or substituted benzyl.

For example, when $R_3$ and $R_4$ of the $L_1$ moiety are both hydrogen there are available the following phenyl or substituted phenyl propionic acids: (o-, m-, or p-)-chlorophenyl-, p-fluorophenyl-, m-(trifluoromethyl)-phenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl there are available, for example, the following 2,2-dimethyl-3-phenyl or substituted phenyl propionic acids: phenyl-and p-methylphenyl.

When one and only one of $R_3$ and $R_4$ is fluoro, there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted benzyl chloride. Thus, the above acid is obtained by the following reaction:

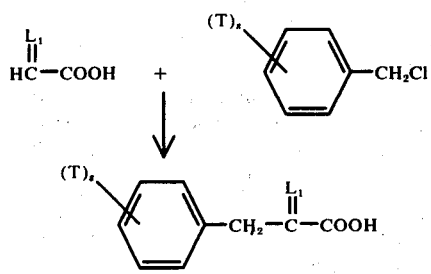

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available 2-methyl alkanoic acids derived from: butyric, pentanoic, hexanoic, heptanoic, and octanoic acids.

For example, when both $R_3$ and $R_4$ of the $L_1$ moiety is fluoro there are available 2,2-difluoro alkanoic acids derived from: butyric, pentanoic, hexanoic, heptanoic, and octanoic acids.

The acids of the above general formula wherein $R_7$ is alkyl and $R_3$ and $R_4$ of the $L_1$ moiety are fluoro are conveniently prepared from the corresponding 2-oxo-alkanoic acids corresponding to butyric, pentanoic, hexanoic, heptanoic, and octanoic acids. The transformation of these 2-oxo-alkanoic acids to the corresponding 2,2-difluoro alkanoic acids proceeds by methods known in the art, using known ketonic fluorinating reagents. For example, $MoF_6 \cdot BF_3$ is advantageously employed in the fluorination.

The formula XXIII compound is prepared from the formula XXII 3-oxo bicyclic lactone by transformation of the 3-oxo-moiety to the $M_5$ moiety.

The above 3-oxo bicyclic lactone is transformed to the corresponding $3\alpha$- or $3\beta$-hydroxy bicyclic lactone, wherein $M_5$ is

or

by reduction of the 3-oxo moiety, followed by separation of the $3\alpha$- and $3\beta$-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium (tri-tert-butoxy)aluminum hydride, metal trialkyl borohydrides, e.g. sodium trimethoxy borohydride, lithium borohydride, and the like. In those cases in which carbon-carbon double bond reduction need not be avoided, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

The 3-oxo bicyclic lactone is transformed into the corresponding (3RS)-3-methyl bicyclic lactone wherein $M_5$ is a mixture of

and

by reaction of the 3-oxo bicyclic lactone with a Grignard reagent, $CH_3 MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC).

The formula XXIV compound is prepared from the formula XXIII compound by deacylation, as described above. The formula XXV compound is then prepared from the formula XXIV compound by replacing any free hydroxy moieties with blocking groups according to $R_{10}$ by the procedure described above. The formula XXVI compound is then prepared from the formula XXV compound by reduction of the formula XXVI lactone to a lactol. Methods known in the art are employed. For example, diisobutylaluminum hydride is employed at -60 to −80° C.

The formula XXVI compound undergoes condensation to form the formula XXVII enol ether. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quarternary phosphonium halide in a base, e.g. butyllithium or phenyllithium, at low temperature, e.g. preferably below −10° C. The formula XXVI lactol is mixed the above reagent and the condensation proceeds smoothly within the temperature range of −30° C. - +30° C. At higher temperatures the reagent is unstable, whereas at low temperatures the rate of condensation is undersirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxy- methylenetriphenylphosphorane. Various hydrocarbyloxymethylenetriphenylphosphoranes which are optionally substituted for the alkoxymethyenetriphenylphosphoranes and are accordingly useful for preparing the formula XXVII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVII enol intermediates are then hydrolyzed to the formula XXVIII lactols. This hydrolysis is done under acidic conditions for example with perchloric acid or acetic acid. Tetrahydrofuran is a suitable diluent for this reaction mixture. Reaction temperatures of time 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXIX compound is then prepared from the formula XXVIII compound by oxidation of the formula XXVIII lactol to a lactone. This transformation is carried out, using for example, silver oxide as an oxidizing reagent, followed by treatment with pyridine hydrochloride and by transformation of any free hydroxy moieties to blocking groups, according to $R_{10}$, following the procedures herein described for these transformations to obtain XXX.

Thereafter the formula XXXI compound or formula XXXII compound (wherein $n$ is 2) is prepared from the formula XXX compound by reduction of the formula XXX lactone to a lactol. For example, diisobutylalminum hydride is employed as is described above for the reduction of lactones to lactols. The formula XXXI lactols are alternately represented by the formula XXVII compound when $n$ is one.

The formula XXXIII compound is prepared from the formula XXXII compound by a Wittig alkylation, using the appropriate ( -carboxyalkyl)triphenylphosphonium bromide. The reaction proceeds as is generally known in the art, by first mixing the appropriate ( -carboxyalkyl)-triphenylphosphonium bromide with sodio dimethyl sulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXIII cis-4,5-didehydro-11-deoxy-PGF$_1$ -, 11-deoxy-PGF$_2$ -, cis-4,5-didehydro-PGF$_1$ -, or PGF$_2$ -type compound.

The formula XXXI V compound is then prepared from the formula XXXIII compound by catalytic hydrogenation of the formula XXXIII compound. Methods known in the art for transformation of PG$_2$-type compounds to PG$_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry, 239, 491 (1974).

The formula XXXII lactol is transformed into the corresponding formula XXXI V 5-oxo-PGF$_1$ -type intermediate first by reduction of the formula XXXII lactol, for example, with aqueous methanolic or ethanolic sodium borohydride to the formula XXXV compound. Alternatively, and preferably, the formula XXXV compound is obtained by a one step reduction of the formula XXV lactone, for example, with lithium aluminum hydride or diisobutyl aluminum hydride at a temperature ranging from 0° to 35° C. For preparing the formula XXXVI compound, a Williams synthesis is employed. For example, the formula XXXV compound is condensed with a haloalkanoate within the scope of $$\text{Hal}-(CH_2)_g-CH_2-COOR_1,$$

wherein Hal is chloro, bromo, or iodo and $g$ is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at −20 to 50° C., but is preferably performed at ambient temperature. Following the condensation the formula XXXVI compound is obtained by methods known in the art, for example, by hydrolysis in cold dilute mineral acid.

Thereafter, the formula XXXVII compound is prepared from the formula XXXIII, XXXI V, or XXXVI compound by oxidation of the 9-hydroxy to a 9-oxo. Oxidation methods known in the art for the transformation of PGF-type compounds to corresponding PGE-type compounds are employed. For example, the Jones reagent or the Collins reagent is advantageously used.

Thereafter the formula XXXVIII is prepared from the formula XXXVII compound by a ring carbonyl reduction. These ring carbonyl reductions are carried out by methods known in the art for ring carbonyl reductions of known prostanoic acid derivatives. See for example, Bergstrom, et al., Arkiv. Kemi. 19,563 (1963), Acta, Chem. Scand. 16, 969 (1962), and British Specification No. 1,097,533. Any reducing agent is used which does not react with carbon-carbon double bonds or ester groups, for example, lithium (tri-tert-butoxy) aluminum hydride, the metal borohydrides (especially sodium, potassium, and zinc borohydride) and the metal trialkoxy borohydrides (e.g. sodium-trimethoxy borohydride) are employed. The PGF - type intermediate is then separated from the mixture of alpha and beta hydroxy reduction products so prepared by methods known in the art for separation of analogous pairs of known isomeric prostanoic acid derivatives. See, for example, Bergstrom, et al. cited above, Granstrom et al., Journal of Biological Chemistry 240, 457 (1965), and Green et al., Journal of Lipid Research 5, 117 (1974). For this purpose silica gel chromatography or high pressure liquid chromatography are employed.

The formula XXXIX compound is then prepared from the formula XXXVIII compound, the formula XXXVII compound, the formula XXXVI compound, the formula XXXIV compound, or the formula XXXIII compound. This preparation proceeds by first separating any mixed C-15 epimers, and thereafter hydrolyzing any blocking groups according to $R_{10}$. Acidic conditions are employed as is described above.

Thereafter the formula XXXIX compound wherein $M_{19}$ is

and $R_8$ is hydroxy is dehydrated under acidic conditions to form the formula XL compound. Methods known in the art for the transformation of PGE-type compounds to PGA-type compounds are employed. For example acetic acid at ambient temperature is advantageously used.

In the employment of the processes above when C-15 tertiary alcohols are to be prepared ($R_5$ is methyl) the use of blocking groups is not required when preparing 11-deoxy-PG's. In the above charts the introduction and hydrolysis of blocking groups are thereby omitted by the preferred process when 11-deoxy-PG-type compounds are prepared.

Certain (3RS)-3-methyl lactones of Chart A may be separated into their respective (3S)- or (3R)-epimers by silica gel chromatographic separation techniques. Where such separation is possible, this route is preferred. Accordingly, in these cases the separation is effected and $M_5$ is

or

and $M_6$ is

or

wherein $R_{10}$ is a blocking group. Accordingly, the separation procedure of PG-type intermediates is omitted when the optional lactone separation is employed.

When a formula XXXIII cis-4,5-didehydro-$PGF_1$ -or cis-4,5-didehydro-11-deoxy-$PGF_1$ -type compound is to be prepared by the procedure of Chart A, the Wittig alkylation step XXXII to XXXIII may be performed on the formula XXVIII lactol, instead of the formula XXXII lactol, thereby eliminating the oxidation, etherification, and reduction steps of Chart A (XXIX through XXXI).

Charts B, C, and D provide methods whereby 3-oxa-3,7-inter-m-phenylene-4,5,6-trinor- or 3,7-inter-m-phenylene-4,5,6-trinor-PG-type intermediates are prepared. With respect to Charts B and C, $R_7$ is preferred to be —$(CH_2)_m$—$CH_3$, or

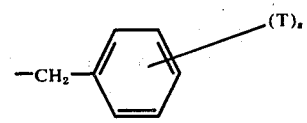

wherein $m$, T, and $s$ are as defined above. In Chart D a method is provided for preparing those novel compounds of this specification wherein $R_7$ is preferably

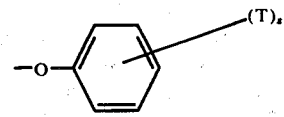

wherein T and s are as defined above, respectively. Accordingly the Charts B-D provide methods whereby intermediates useful in producing all inter-m-phenylene-PG-type intermediates are prepared.

In Chart B both the endo and exo forms of bicyclo hexene LXI are available or are made by methods known in the art, in either their racemic or enantiomerically pure forms. See U.S. Pat. No. 3,711,515. Either the endo or exo starting material will yield the ultimate intermediates of formula LXXIII by the process of Chart B.

Oxetane LXII is obtained by reaction of the formula LXI bicyclo hexene with an aldehyde of the formula

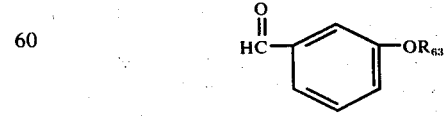

wherein $R_{63}$ is carboxyacyl of the formula

wherein $R_{64}$ is hydrogen, alkyl of one to 19 carbon atoms, inclusive, or aralkyl of 7 to 12 carbon atoms, inclusive, wherein alkyl or aralkyl are substituted with zero to 3 halo atoms.

The above benzaldehydes are available or readily prepared by methods known in the art. Examples of such compounds within this scope are:

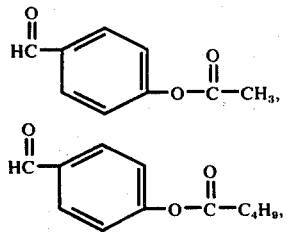

and

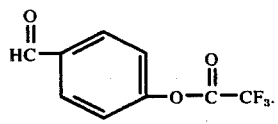

The formation of oxetane LXII is accomplished by photolysis of a mixture of the bicyclo hexene and the aldehyde in a solvent. The bicyclo hexene is preferably used in excess over the molar equivalent, for example 2 to 4 times the stoichiometric equivalent amount. The solvent is a photochemically inert organic liquid, for example liquid hydrocarbons, including benzene or hexane, 1,4-dioxane, and diethyl ether. The reaction is conveniently done at ambient conditions, for example 25° C., but may be done over a wide range of temperature, from about −78° C. to the boiling point of the solvent. The irradiation is done with mercury vapor lamps of the low or medium pressure type, for example those peaking at 3500 A. Such sources are available from The Southern New England Ultraviolet Co., Middletown, Conn. Alternatively, those lamps which emit a broad spectrum of wavelengths and which may be filtered to transmit only light of λ ~ 3000–3700 A may also be used. For a review of photolysis see D. R. Arnold in "Advances in Photochemistry", Vol. 6, W. W. A. Noyes et al., Wiley-interscience, New York, 1968, pp. 301–423.

The cleavage of the oxetane ring to yield the formula LXIII compound from the formula LXII compound is accomplished with an alkali metal in the presence of a primary amine or an alcohol. Preferred is lithium in ethylamine, or sodium in butyl alcohol. See L. J. Altman et al., Synthesis 129 (1974). The cleavage transformation may also be accomplished by catalytic hydrogenation over an inert metal catalyst, e.g. Pd-on-carbon, in ethyl acetate or ethanol.

The formula LXIV compound is prepared from the formula LXIII diol by preferably blocking the two hydroxyl groups with carboxyacyl groups according to $R_{63}$, i.e.

as defined above. For example, the diol is treated with an acid anhydride such as acetic anhydride, or with an acyl halide in a tertiary amine. Especially preferred is pivaloyl chloride in pyridine.

Other carboxyacylating agents useful for this transformation are known in the art of readily obtainable by methods known in the art, and include carboxyacyl halides, preferably chlorides, bromides, or fluorides, i.e. $R_{63}C(O)Cl$, $R_{64}C(O)Br$, or $R_{64}C(O)F$, and carboxy acid anhydries, $(R_{64}C-)$ hd 2O, wherein $R_{64}$ is as defined above. The preferred reagent is an acid anhydride. Examples of acid anhydrides useful for this purpose are acetic anhydride, propionic anhydride, buyric anhydride, pentanoic anhydride, nonanoic anhydride, trideconoic anhydride, steric anhydride, (mono, di, or tri)chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 to 3)-phenylpropionic anhydride, 13-phenyltridecanoic anhydride, phenoxyacetic anhydride, benzoic anhydride, (o, m, or p)-bromobenzoic anhydride, 2,4-(or 3,4)-dichlorobenzoic anhydride, p-trifluoromethylbenbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 5)-biphenylcarboxylic anhydride, 3-chloro-4-biphenylcarboxylic anhydride, 5-isopropyl-6nitro-3-biphenylcarboxylic anhydride, and (1 or 2)-naphthoic anhydride. The choice of anhydride depends upon the identity of $R_{64}$ in the final acylated product, for example when $R_{64}$ is to be methyl, acetic anhydride is used; when $R_{64}$ is to be 2-chlorobutyl, 3-chlorovaleric anhydride is used.

When $R_{64}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, the formula LXIII diol is reacted with two equivalents of sodium hydride and then with excess ethyl formate.

In formula LXIV, $R_{68}$ may also represent a blocking group including benzoyl, substituted benzoyl, monoesterified phthaloyl and substituted or unsubstituted naphthoyl. For introducing those blocking groups, methods known in the art are used. Thus, an aromatic acid of the formula $R_{63}OH$, wherein $R_{63}$ is as defined above, for example benzoic acid, is reacted with the formula LXIII compound in the presence of a dehydrating agent, e.g. zinc chloride; or an anhydride of the aromatic acid of the formula $(R_{63})_2O$, for example benzoic anhydride, is used.

Preferably, however, an acyl halide e.g. $R_{63}Cl$, for example benzoyl chloride, is reacted with the formula-LXII compound in the presence of a tertiary amine such as pyridine, triethylamine, and the like. The reaction is carried out under a variety of conditions using procedures generally known in the art. Generally, mild conditions are are employed, e.g. 20°–60° C., contacting the reactants in a liquid medium, e.g. excess pyridine or an inert solvent such as benzene, toluene, or chloroform. The acylating agent is used either in stoichiometric amount or in excess.

As examples of reagents providing $R_{63}$ for the purposes of this invention, see the discussion above pertaining to the use of acyl protecting groups.

The formula LXIV acetal is converted to aldehyde LXV by acid hydrolysis, known in the art, using dilute aqueous mineral acids, acetic or formic acids, and the like. Solvents such as acetone, dioxane, and tetrahydrofuran are used.

For the conversion of LXV to LXIX, it is optional whether $R_{66}$ be hydrogen or a "blocking group" as defined below. For efficient utilization of the Wittig reagent it is preferred that $R_{66}$ be a blocking group. If the formula LXIV compound is used wherein $R_{68}$ is hydrogen, the formula LXV intermediate will have hydrogen at $R_{66}$. If $R_{66}$ is to be a blocking group, that may be readily provided prior to conversion of LXV to LXVI by reaction with suitable reagents as discussed below.

The blocking group, $R_{65}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{63}$ above, i.e. acetyl, and also benzoyl, naphthoyl, and the like; (b) blocking groups according to $R_{10}$; and (c) $-Si(G_1)_3$ wherein $G_1$ is as defined above.

In replacing the hydrogen atoms of the hydroxyl groups with a carboxyacyl blocking group, methods known in the art are used. The reagents and conditions are discussed above for $R_{68}$ on the compound of formula LXIV.

When the blocking group is according to $R_{10}$ appropriate reagents and conditions are as defined above.

When the blocking group is silyl of the formula $-Si(G_1)_3$, the formula LXV compound is transformed to a silyl derivative of formula LXV by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Silicon Compounds," Reinhold Publishing Corp., New York, N. Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotrim-tolysilane, and tribenzylchlorosilane. Alternatively, a chlorosilane is used with a corresponding disilazane. Examples of other silylating agents suitable for forming the formula LXV intermediates include pentamethylsilylamine, pentaethylsilylamine, N-trimethylsilyldiethylamine, 1,1,1-triethyl-N,N-dimethylsilylamine, N,N-diisopropyl-1,1,1,-trimethylsilylamine, 1,1,1-tributyl-N,N-dimethylsilylamine N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In transforming the formula LXV compound to the formula LXVI compound the aldehyde group is transformed by the Wittig reaction to a moiety of the formula

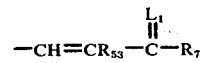

For this purpose a phosphonium salt prepared from an organic chloride or bromide of the formula

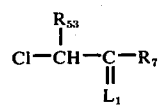

or

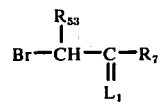

is employed, wherein $L_1$, $R_7$, and $R_{53}$ are as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and references cited therein.

The formula LXVII compound is obtained by deblocking if necessary. When $R_{66}$ is a hindered carboxyacyl, $R_{66}$ on the phenolic hydroxy is selectively replaced with hydrogen by hydrolysis with sodium or potassium hydroxide or carbonate ethanol-water. Other water-miscible solvents may be substituted, for example 1,4-dioxane, tetrahydrofuran, or 1,2-dimethoxyethane. The selective hydrolysis is preferably carried out at −15° to 25° C. Higher temperatures may be used but with some decrease in selectivity.

Total hydrolysis of $R_{66}$ blocking groups on the formula LXVI compound is accomplished, when $R_{66}$ is carboxyacyl, with an alkali alkoxide in an alcoholic solvent, preferably sodium methoxide in methanol at a temperature from 25° C. to 50° C. When $R_{66}$ is trialkylsilyl, either aqueous acid or base are used at 25° to 50° C.

Continuing with Chart B, a Williamson synthesis is employed to obtain the formula LXVIII compound. The formula LXVII phenol is condensed with a haloalkanoate within the scope of $Hal-(CH_2)_g-COOR_1$ wherein Hal is chloro, bromo, or iodo and $g$ and $R_1$ are as defined above. Preferably, however, the reaction proceeds by the Method of Chart A for preparing 5-oxa-PG-type compounds, i.e., the transformation of XXXV to XXXVI.

The transformation of the formula LXVIII compound to the formula LXIX is accomplished by any one of several routes known in the art. See U.S. Pat. No. 3,711,515. Thus, the alkene LXVIII is hydroxylated to glycol LXIX. For this purpose osmium tetroxide is a suitable reagent, for example in conjunction with N-methylmorpholine oxidehydrogen peroxide complex (see Fieser et al., "Reagents for Organic Synthesis", p.

690, John Wiley and Sons, Inc., New York (1967)). Thereafter, several methods are available for obtaining the formula LXX product. In one method the glycol is converted to a bis(alkanesulfonic acid) ester and subsequently hydrolyzed to the formula LXX compound by methods known in the art (See, for example German Offenlegungsschrift No. 1,936,676, Derwent Farmdoc No. 6862R). Another method is by way of a diformate by formolysis of of the glycol (see U.S. Pat. No. 3,711,515).

Still another method is by way of a cyclic ortho ester. For this purpose, glycol LXIX is reacted with an ortho ester of the formula

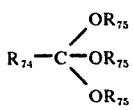

wherein $R_{74}$ is hydrogen, alkyl of one to 19 carbon atoms, inclusive, or aralkyl of 7 to 12 carbon atoms, inclusive, substituted with zero to 3 halo atoms; and $R_{75}$ is methyl or ethyl. THere is then formed a cyclic orthoester of the formula

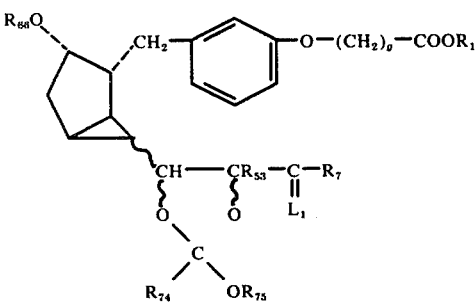

wherein g, $R_1$, $R_{53}$, $R_{66}$, $R_{74}$, $R_{75}$, $L_1$ and $R_7$ are as defined above. The reaction goes smoothly in a temperature range of −50° C. to +100° C., although for convenience 0° C. to +50° C. is generally preferred. From 1.5 to 10 molar equivalents of the ortho ester are employed, together with an acid catalyst. The amount of the catalyst is usually a small friction of the weight of the glycol, e.g., about 1%, and typical catalysts include pyridine hydrochloride, formic acid, hydrogen chloride, p-toluenesulfonic acid, trichloroacetic acid, or trifluoracetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
triethyl orthoacetate,
triethyl orthopropionate,
trimethyl orthobutyrate,
trimethyl orthovalerate,
trimethyl orthooctanoate,
trimethyl orthophenylacetate, and
trimethyl ortho (2,4-dichlorophenyl)acetate.

Preferred are those ortho esters wherein $R_{74}$ is alkyl of one to 7 carbon atoms; especially preferred are those wherein $R_{74}$ is alkyl of one to 4.

Next, the cyclic orthoester depicted above is reacted with anhydrous formic acid to yield a diol diester of the formula

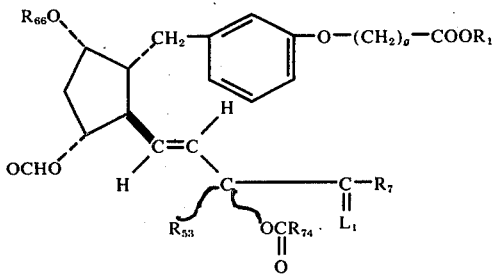

wherein g, $R_1$, $R_7$, $R_{53}$, $R_{66}$, and $L_1$ are as defined above.

Anhydrous formic acid refers to formic acid containing not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°-30° C. and is usually completed within about 10 minutes.

Finally, the diol diester above is converted to product LXX by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from −50° C. to 100° C. The time for completion of the reaction varies with the nature of $R_{74}$ and the base, proceeding in the case of alkali carbonates in a few minutes when $R_{74}$ is a hydrogen but taking up to several hours when $R_{74}$ is ethyl, for example.

When the solvolysis proceeds too long or when conditions are too severe, an ester group ($R_1$) is often removed. They are, however, readily replaced by methods known in the art. See the discussion below.

The formula LXXIII compound is prepared from the formula LXX compound by separation of any mixed C-15 epimers. Such separation proceeds by methods discussed in the preceding Chart for accomplishment of this purpose (e.g., thin layer chromatography or high pressure liquid chromatography).

Referring to Chart C, there are shown process steps by which the formula LXXVI bicyclo hexene is transformed first to an oxetane (Formula LXXVII) with a fully developed side chain, e.g.,

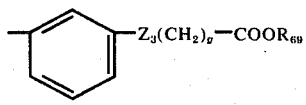

wherein $Z_3$ is oxa or methylene and ultimately to the formula LXXXIV compound. In chart C, $R_{69}$ is hydrogen or alkyl of one to 4 carbon atoms, inclusive, and $R_{70}$ is hydrogen, alkyl of one to 4 carbon atoms, inclusive, or silyl of the formula 1a $(G_1)_3Si$- wherein $G_1$ is as defined herein above.

In transforming LXXVI to LXXVII in Chart C, there is employed an aldehyde of the formula

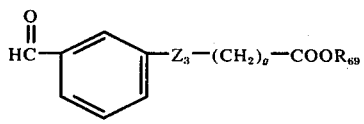

wherein $Z_3$ and $R_{69}$ are as defined above. Such aldehydes are available or are readily prepared by methods known in the art, e.g.,

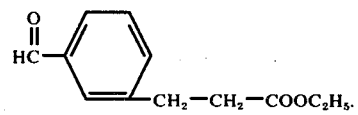

The conditions for this transformation are essentially the same as for the corresponding step of Chart B (i.e., LXI to LXII). Thereafter, the preparation of the formula LXXXI compound proceeds by methods analogous to the corresponding steps of Chart B (i.e., LXII to LXVI) with the preference that LXXVII to LXXVIII is accomplished catalytically.

The steps transforming LXXI to LXXIV then proceed in similar fashion, employing the same or similar reagents and conditions as the corresponding steps of Chart B discussed above.

As discussed above, Chart D provides a method whereby the formula XCI PG-type intermediate, prepared according to Chart B or Chart C is transformed to the corresponding formula XCIV 16-phenoxy-PG-type intermediates.

The formula XCII compound is prepared from the formula XCI compound by cleavage of the 13,14-trans double bond, conveniently by ozonolysis. Ozonolysis proceeds by bubbling dry oxygen, containing about 3 percent ozone, through a mixture of a formula XCI compound in a suitable nonreactive diluent. For example, n-hexane is advantageously employed. The ozone may be generated using methods known in the art. See, for example, Fieser, et al., "Reagents for Organic Synthesis," John Wiley and Sons, Inc. (1967), pages 773–777. Reaction conditions are maintained until the reaction is shown to be complete, for example, by silica gel thin layer chromatography or when the reaction mixture no longer rapidly decolorizes a dilute solution of bromine in acetic acid.

The formula XCIII compound is then prepared from the formula XCII compound by blocking with an $R_{65}$ blocking group and thereafter employing a phosphonate of the formula:

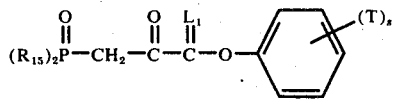

wherein $R_{15}$, $L_1$, T, and s are as defined above. Phosphonates of this general formula are prepared by methods known in the art. See the text hereinabove accompanying Chart A for discussion of the preparation and the appropriate reaction conditions by which the Wittig reaction proceeds. The formula XCIV compound is prepared from the formula XCIII compound by transformation of the 15-oxo moiety to an $M_1$ moiety. Methods hereinabove, particularly those discussed in Chart A above, are employed.

Optionally the method of Chart D is used to introduce the various other $R_7$ moieties to the formula XCII compound using the appropriate phosphonate.

Chart E provides a method whereby the formula CI PGF -type product prepared above is transformed to the corresponding CIX formula PGD-type compound; formula 9-deoxy-9,10-didehydro-PGD-type compound; or formula CXV 9-deoxy-PGD-type compound.

The formula CII compound is prepared from the formula CI compound by cycloalkylboronization when and only when $R_5$ is hydrogen. Accordingly, the bicyclic formula CII compound is prepared by reaction of the formula CI compound with a slight stoichiometric excess of an alkylboronic acid. The course of the reaction is conveniently monitored by silica gel thin layer chromatography and the reaction is preferably carried forth under vigorous stirring at reflux temperatures. The preferrred reaction diluent for this transformation is methylene chloride, through other suitable organic solvents are likewise employed. The formula CII compound so formed is then etherified by replacing the free hydroxy hydrogen of the $M_1$ moiety with a blocking group according to $R_{10}$. Procedures hereinabove described are advantageously employed. Thereafter the formula CIV compound, which is represented by formula CI when $R_5$ is methyl, is prepared from the formula CIII compound by decycloboronization. For this purpose an alkali metal hydroxide (e.g., sodium, lithium, or potassium hydroxide) is combined with the formula CIII compound in a water-miscible diluent capable of yielding a homogeneous reaction mixture (e.g., methanol or ethanol), and the resulting solution thereafter treated with dilute aqueous hydrogen peroxide. The formula CIX compound is then prepared from the formula CIV compound by one of two methods.

By the first method the formula CIV compound is selectively oxidized at the C-11 over the C-9 position using, for example, the Jones reagent. In order to achieve high selectivity, it is desirable that the reaction be carried out at between −20 and −60° C. Especially preferred are reaction temperatures between −55 and −40° C. Accordingly, upon separation of mixtures of product, the pure formula CXI PGD-type intermediate is obtained.

By the second procedure the formula CIX compound is prepared from the formula CIV compound by first selectively silylating the C-11 hydroxy of the formula CIV compound over the C-9 hydroxy. Silyl groups according to the formula $-Si-(G_1)_3$ are advantageously employed. For selective monosilylation procedures see U.S. Pat. No. 3,822,303, issued July 2, 1974, German Offenlegungschrift 2,259,195, Derwent Farmdoc CPI 36457U-B or Netherlands Pat. No. 7,214,142, Derwent Farmdoc CPI 26221U-B. Thereafter the silylated compound so formed (formula CV) is transformed to the corresponding C-9 ether (formula CVI), employing blocking groups according to $R_{10}$, in place of the 9-hydroxy hydrogen. Thereafter the C-11 silyl moiety is hydrolyzed by methods hereinabove described and the resulting 11-hydroxy compound (formula CVII) oxidized by the procedure described above, yielding the corresponding 11-oxo compound (formula CVIII).

Thereafter, the formula CIX compound is prepared from this 11-oxo compound (formula CVIII or CXI) by replacing any blocking groups according to $R_{10}$ with hydrogen. Methods described hereinabove are employed.

Additionally Chart E provides a method whereby formula CIX or CXI PGD-type compound is transformed variously into the formula CX or CXII 9-deoxy-9,10-didehydro-PGD-type compound, respectively, the formula CXV 9-deoxy-PGD-type compound.

The formula CX or CXII compound is prepared, respectively, from the formula CIX or CXI compound by mild acid catalyzed dehydration of the formula CIX or CXI compound. Organic acids such as acetic acid, trifluoroacetic acid, citric acid, oxalic acid, or p-toluenesulfonic acid are useful for this purpose. Diluents such as tetrahydrofuran, methanol, ethanol, or water are usefully employed. Preferably, however, a diluent is employed which will result in a homogeneous reaction mixture. The dehydration proceeds rapidly at temperatures between ambient temperature and 40° C. Alternatively, a formula CIX or CXI compound is left standing on a column of acid washed silica gel, thereby dehydrating to the formula CX or CXII compound usually within one to 5 days. The formula CXIII is thereafter prepared from the CXII compound by reduction of the formula CXII compound. This reduction selectively reduces the endocyclic double bond and transforms the 11-oxo to an 11-hydroxy, without affecting side chain unsaturation. For this purpose, an alkali metal borohydride, e.g. sodium, potassium, or lithium borohydride is effectively employed in aqueous alcoholic solution. The reaction is carried out at about −20° C. and is ordinarily complete within a few minutes. The formula CXIV compound is then prepared by one of two methods.

The formula CXII compound is optionally converted into the formula CXIV compound by selective catalytic hydrogenation of the endocyclic double bond. This transformation is selectively effective without affecting side chain unsaturation. For this purpose the 5 to 10 percent palladium or rhodium catalyst on carbon, alumina, or other suitable support is employed. The reaction is carried out in any suitable organic solvent, e.g. ethyl acetate, methanol, ethanol, or diethyl ether, at temperatures of between −30 and 50° C. and pressures greater than or equal to atmospheric pressure.

Alternatively the formula CXIV compound is prepared from the formula CXIII compound by oxidation as described above in the transformation of the formula CIV compound to the formula CXI compound. For this purpose an oxidizing agent such as the Jones reagent (acidified chromic acid) is employed. See for reference, Journal of the Chemical Society 39 (1946). A slight stoichiometric excess beyond the amount necessary to oxidize the secondary hydroxy group of the formula CXIII compound is employed. Acetone is a useful diluent for this purpose. Reaction temperatures at least as low as about 0° C. are useful. Preferred reaction temperatures are in the range of −10 to −50° C. An especially useful reagent for this purpose is the Collins reagent (chromium trioxide in pyridine). See for reference J. C. Collins, et al., Tetrahedron Letters 3363 (1968). Dichloromethane is a suitable diluent for this purpose. Reaction temperatures below 30° C. are preferred. Reaction temperatures in the range of about −10 to +10° C. are especially preferred. The oxidation proceeds rapidly and is ordinarily complete within several minutes. Pure product is then isolated by conventional means, e.g. silica gel chromatography.

Examples of other oxidation agents useful for this transformation are mixtures of chromium trioxide in pyridine (Journal of the American Chemical Society 75, 422 (1953)), and tert-butyl chromate in pyridine (Biological Chemistry Journal, 84, 195 (1962)), mixtures of sulfur trioxide in pyridine and dimethyl sulfoxide (Journal of the American Chemical Society 89, 5505 (1967)), and mixtures of dicyclohexylcarbodiimide and dimethylsulfoxide (Journal of the American Chemical Society 87, 5661 (1965)).

Thereafter the formula CXV compound is prepared from the formula CXIV compound by hydrolysis of blocking groups according to $R_{10}$, as described hereinabove.

Chart F provides a method whereby the PG-type intermediates prepared in Charts A-E are transformed to the corresponding 2-decarboxy-2-hydroxymethyl-PG-type compounds of the present invention.

The present transformation (CXXI to CXXII) proceeds by reduction of the carboxylic acid or ester with reagents known to reduce carboxylic acids to corresponding primary alcohols. For example, when the formula CXXI compound is an acid or an ester, the reduction proceeds with lithium aluminum hydride or diisobutylaluminum hydride.

Useful solvents include diethyl ether, tetrahydroguran, dimethoxyethane, or like organic solvents. The reaction is conveniently run at temperatures of about −78° C. to 100° C., although preferably at about 0° C. to 50° C. When the formula CXXI compound is an acid, reducing agents such as diborane are also employed when double bond reduction is not a problem.

When the formula CXXI compound contains a carbonyl function on the cyclopentane ring, the reduction described in the preceeding paragraph frequently reduces that carbonyl to the corresponding alcohol. Thus, the preparation of the formula CXXII compound in this case requires oxidation of the hydroxy so produced to a corresponding oxo compound. In this case, it is desirable to first provide protection for the carbonyl by its transformation to a corresponding oxime, ethylene ketal, or similar carbonyl derivative before the reduction of the carboxylic acid is attempted. Thereafter, the protected carbonyl derivative is removed, preparing the formula CXXII product. Introduction and removal of these carbonyl protecting groups is accomplished by methods known in the art.

Alternatively, the formula CXXI PGF-type compound is transformed first to the corresponding 2-decarboxy-2-hydroxymethyl-PGF-type compound and then 2-decarboxy-2-hydroxymethyl-PGE-, PGA-, PGD-, 9-deoxy-PGD-, 9,10-didehydro-9-deoxy-PGD-type compound following the procedure described in Charts A-E above for transforming PGF-type compounds to PG-type compounds of the various cyclopentane ring structures described herein. Likewise, the corresponding formula CXXI 11-deoxy-PGF-type compound is transformed to an 11-deoxy-2-decarboxy-2-hydroxymethyl-PGF-type compound and thereafter to the corresponding formula CXXII 11-deoxy-PGE or 11-deoxy-PGF -type compounds. Further, when PGE-type compounds are to be prepared from PGA-, or 11-deoxy-PGE-, or PGE-type compounds, it is preferred to use in place of the formula CXXI compound the corresponding formula CXXIII, CXXXIV, or CXXXVI PGF-type compound which is optionally etherified.

By another route the PGE-type product is prepared from the 2-decarboxy-2-hydroxymethyl-PGF-type starting material by first selectively silylating at C-1, C-11 and C-15 (where $R_5$ is hydrogen) over C-9, and then oxidizing and hydrolyzing the silyl groups. Methods known in the art are employed.

Chart G provides a method whereby the formula CXXXI lactol intermediate of Chart A is transformed to the various 2-decarboxy-2-hydroxymethyl PG-type products disclosed herein. The formula CXXXII compound is prepared from the formula CXXXI compound employing the method described in Chart A for the preparation of the formula XXXIII compound from the formula XXXII compound except that a Wittig reagent prepared from a corresponding ( -tetrahydropyranyloxymethylalkyl)triphenylphosphonium bromide is used in place of the ( -carboxyalkyl)triphenylphosphonium bromide of Chart A. Alternatively, and preferably when PGF- or 11-deoxy-PGF-type products are to be prepared, an ( -hydroxymethylalkyl)triphenylphosphonium bromide is employed in this Wittig alkylation. Thereafter, the formula CXXXIV PGE or 11-deoxy-PGE-type compound is prepared from the PGF-type compound by oxidation, employing for example the Jones reagent or Collins reagent as described above. Thereafter, the formula CXXXV compound wherein $M_{18}$ is

is prepared from the formula CXXXIV compound by ring carbonyl reduction followed by separation of the 9-hydroxy epimers (employing methods hereinabove described), hydrolysis of any blocking groups, and separation of any mixed C-15 epimers. The hydrolysis of the blocking groups and separation of the epimers proceeds by methods hereinabove described. Alternatively, the formula CXXXV compound is prepared from the formula CXXXII compound or formula CXXXIII compound by hydrolysis of the blocking groups followed by separation of any mixed C-15 epimers as described above. Thereafter, the formula CXXXVI compound is prepared from the formula CXXXV compound wherein $M_{18}$ is

and $R_8$ is hydroxy by acidic dehydration employing methods hereinabove described.

The transformations of Chart H provide a method whereby the 2-decarboxy-2-hydroxymethyl-PGF -type compounds of formula CXXXVII are transformed to the corresponding 2-decarboxy-2-hydroxymethyl-PGD-, 9-deoxy-PGD-, or 9,10-didehydro-9-deoxy-PGD-type products. These transformations follow the method described in Chart E for the preparation of corresponding carboxylic acids.

Accordingly, the formula CXXXVIII compound is prepared from the formula CXXXVII compound by the method described in Chart E for the preparation of the formula CIV compound from the formula CI compound. Thereafter the formula CXXXIX compound is prepared from the formula CXXXVIII compound by the method described for the preparation of the formula CIX compound from the formula CIV compound.

Further, the formula CXL compound is prepared by the method described for the preparation of the formula CX compound from the formula CIX compound. Finally, the formula CXLI compound is prepared from the formula CVIII compound by the method described above for the preparation of the formula CXV from the formula CXI compound.

In all of the above described reactions, the products are separated by conventional means from starting material and impurities. For example, by use of silica gel chromatography monitored by thin layer chromatography the products of the various steps of the above charts are separated from the corresponding starting materials and impurities.

Finally, the various hydroxy-containing PG-type products are optionally carboxyacylated. The reaction time for carboxyacylation will depend on such factors as the reaction temperature, and the nature of the anhydride and tertiary amine reactants. With acetic anhydride, pyridine, and a 25° C. reaction temperature, a 6 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer on deuterochloroform solutions with tetramethylsilane as an internal standard (downfield).

Mass spectra are recorded on an CEG model 110B Double Focusing High Resolution Mass Spectrometer or an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1

Dimethyl 3,3-dimethyl-2-oxo-4-phenylbutylphosphonate,

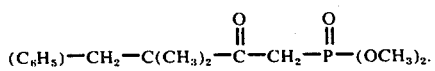

A. To a solution of 101.2 g. of diisopropylamine in 125 ml. of tetrahydrofuran under nitrogen at 0° C. is added dropwise with cooling (using an ice-methanol bath) 625 ml. of 1.6 molar n-butyllithium in hexane. To the resulting solution is added dropwise with cooling 46.5 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hr. This stirred mixture is then diluted with diethyl ether and excess cold dilute hydrochloric acid. The organic layer is washed with saline and thereafter dried, concentrated, and the residue distilled under vacuum. Accordingly, there is prepared 2,2-dimethyl-3-phenyl propionic acid.

B. A mixture of 48 g. of the product of part A of this example and 82 g. of thionyl chloride are heated with stirring on a steam bath for 2 hr. The mixture is then concentrated under vacuum. Thereafter dry benzene is added and the resulting mixture is concentrated again, removing all traces of thionyl chloride. Distillation of this residue yields 48.2 g. of 2,2-dimethyl-3-phenylpropionyl chloride.

C. To a solution of 63 g. of dimethylmethylphosphonate in 600 ml. of tetrahydrofuran under nitrogen at −75° C. is added with stirring 312 ml. of 1.6 molar n-butyllithium in hexane. The addition rate is adjusted so that the reaction temperature remains below −55° C. Ten minutes after the addition is complete, 48.2 g. of the reaction product of part B of this example and 50 ml. of tetrahydrofuran are added dropwise at such rate as to maintain the reaction temperature below −60° C. The resulting mixture is then stirred at −75° C. for 2 hr. and then ambient temperature overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute sodium bicarbonate solution. The organic layer is then washed with brine, dried, and concentrated. The residue was crystallized from diethyl ether, yielding 54 g. of dimethyl 3,3-dimethyl-2-oxo-4-phenylbutylphosphonate (8.0 g.), the title compound. The melting point is 48°–50° C.

Following the procedure of Example 1, but using in place of benzyl chloride substituted benzyl chlorides of the formula

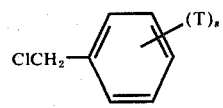

wherein T is fluoro, chloro, trifluoromethyl, alkyl of one to 3 carbon atoms, inclusive, or alkoxy of one to 3 carbon atoms, inclusive, and wherein s is zero, one, 2, or 3, with the proviso that not more than two T's are other than alkyl, and with the further proviso that the various T's may be the same or different, there are prepared the corresponding dimethyl-3,3-dimethyl-2-oxo-4-(substituted phenyl)butylphosphonates. For example, there is prepared by this procedure dimethyl 3,3-dimethyl-2-oxo-4-(p-fluorophenyl)butylphosphonate.

Further, following the procedure of Example 1, but using in place of the isobutyric acid of Example 1, part A, propionic acid, there is prepared dimethyl 3-methyl-2-oxo-4-phenylbutylphosphonate. Following the procedure of Example 1, but using the substituted benzyl chlorides described above in place of benzyl chloride and propionic acid in place of isobutyric acid there are prepared the various dimethyl 3-methyl-2-oxo-4-(substituted phenyl)-butylphosphonates wherein the phenyl substitution is as described above.

Further, following the procedure of Example 1, but using acetic acid in place of isobutyric acid as used in Example 1, part A, there is prepared dimethyl-2-oxo-4-phenylbutylphosphonate. Using acetic acid in combination with the various substituted benzyl chlorides described above according to the procedure of Example 1, there are prepared the various dimethyl 2-oxo-4-(substituted phenyl)butyl phosphonates, wherein the phenyl substitution is as described above.

Following the procedure of Example 1, but using 2,2-difluoroacetic acid in place of isobutyric acid as used in part A of Example 1, there is prepared dimethyl 3,3-difluoro-2-oxo-4-phenylbutylphosphonate. Further, following the procedure of Example 1, but using 2,2-difluoro acetic acid in combination with substituted benzyl chlorides described above, there are prepared the corresponding dimethyl 3,3-difluoro-2-oxo-4-substituted phenylbutylphosphonate, wherein the phenyl substitution is as described above.

Further, following the procedure of Example 1, but using 2-fluoro acetic acid in place of isobutyric acid there is prepared dimethyl 3-fluoro-2-oxo-4-phenylbutylphosphonate.

Using 2-fluoro acetic acid and the various substituted benzyl chlorides described above according to the procedure of Example 1, there are prepared the various dimethyl 3-fluoro-2-oxo-4-(substituted phenyl)butyl phosphonates, wherein the phenyl substitution is as described above.

EXAMPLE 3

(6-Carboxyhexyltriphenylphosphonium bromide)

A mixture of 63.6 g. of 7-bromoheptanoic acid, 80 g. of triphenylphosphine, and 30 ml. of acetonitrile, is refluxed for 68 hr. Thereafter 200 ml. of acetonitrile is removed by distillation. After the remaining solution is cooled to room temperature, 300 ml. of benzene is added with stirring. The mixture is then allowed to stand for 12 hr. A solid separates which is collected by filtration, yielding 134.1 g. of product, melting point 185°–187° C.

Following the procedure of Example 3, but using 3-bromopropionic acid, 4-bromobutanoic acid, 5-bromopentanoic acid, or 6-bromohexanoic acid, in place of 7-bromoheptanoic acid, there are prepared the corresponding (ω-carboxyalkyl)triphenylphosphonium bromides.

Following the procedure of Example 3, but using an ω-bromo-alkan-1-ol in place of the ω-bromo alkanoic acid, there is prepared a corresponding (ω-hydroxymethylalkyl) triphenylphosphonium bromide.

EXAMPLE 4

3α-Benzoyloxy-5α-hydroxy-2β-(3-oxo-4,4-difluoro-trans-1-octenyl)-1α-cyclopentaneacetic acid, γ lactone (Formula XXII: $R_7$ is n-butyl, $R_{16}$ is benzoyloxy, $R_3$ and $R_4$ of the $L_1$ moiety are fluoro.

Refer to Chart A.

A. A solution of 24.3 g. of thallous ethoxide in 125 ml. of dry benzene is cooled in an ice bath, and thereafter a solution of 25.3 g. of methyl 3,3-difluoro-2-oxoheptylphosphonate in 75 ml. of benzene is added and thereafter rinsed with 50 ml. of benzene. The solution is stirred for 30 min. at 5° C. and thereafter 22.1 g. of crystalline 3α-benzoyloxy-5α-hydroxy-2β-carboxaldehyde-1α-cyclopentaneacetic acid, γ lactone is added rapidly. This reaction mixture is then stirred for 13 hr. at ambient temperature yielding a brown solution of pH 9-10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields 20.3 g. of crude product, which upon recrystallization from 240 ml. of diethyl ether in pentane (2:1) yields 13.3 g. of 3α-benzoyloxy-5α-hydroxy-2β-(3-oxo-4,4-difluoro-trans-1-octenyl)-1α-cyclopentaneacetic acid, γ lactone.

Alternatively this product is prepared by adding 3α-benzoyloxy-2β-carboxaldehyde-5α-hydroxy-1α-cyclopentaneacetic acid γ lactone (3 g.) in 30 ml. of dichloromethane to a solution of dimethyl 2-oxo-3,3-difluoroheptylphosphonate (6.69 g.) and sodium hydride (1.35 g.) in 15 ml. of tetrahydrofuran. The resulting reaction mixture is then stirred for 2 hr. at about 25° C., acidified with acetic acid, and concentrated under reduced pressure. The residue is partitioned between dichloromethane and water, and the organic phase is concentrated. The residue is chromatographed on silica gel, eluted with ethyl acetate in Skellysolve B (1:1).

Following the procedure of Example 4, but using in place of 3α-benzoyloxy-5α-hydroxy-2β-carboxaldehyde-1α-cyclopentaneacetic acid γ lactone, 5α-hydroxy-2β-carboxaldehyde-1α-cyclopentaneacetic acid γ lactone, there is obtained 5α-hydroxy-2β-(3-oxo-4,4-difluoro-trans-1-octenyl)-1α-cyclopentaneacetic acid γ lactone. Further, following the procedure of Example 4, but using in place of dimethyl 2-oxo-3,3-difluoroheptylphosphonate, any of the various dimethyl phosphonates described hereinabove there are prepared the corresponding 3α-benzoyloxy-5α-hydroxy-1α-cyclopentaneacetic acid γ lactones or 5α-hydroxy-1α-cyclopentaneacetic acid γ lactones with a 2β-(3-oxo-trans-1-alkenyl)-substituent, optionally substituted, as follows:

4,4-difluorohexenyl; 4,4-difluoroheptenyl; 4,4-difluorononenyl; 4,4-difluorodecenyl; 4-fluorohexenyl; 4-fluoroheptenyl, 4-fluorooctenyl; 4-fluorononenyl; 4-fluorodecenyl; 4,4-dimethylhexenyl; 4,4-dimethylheptenyl, 4,4-dimethyloctenyl; 4,4-dimethylnonenyl; 4,4-dimethyl-decenyl; 4-methylhexenyl; 4-methylheptenyl, 4-methyloctenyl, 4-methylnonenyl; 4-methyldecenyl; hexenyl, heptenyl; octenyl; nonenyl; decenyl; 5-phenylpentenyl; 5-(m-trifluoromethylphenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5(p-chlorophenyl)-pentenyl; 4-methyl-5-phenylpentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl; -4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-(m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4-fluoro-5-(m-chlorophenyl)-pentenyl; 4-fluoro-5-(p-trifluoromethylphenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4(p-fluorophenoxy)-butenyl; 4-(p-chlorophenoxy)-butenyl; 4-methyl-4-phenoxy-butenyl; 4-methyl-4-(m-trifluoromethylphenoxy)-butenyl; 4-methyl-4-(m-fluorophenoxy)-butenyl; 4-methyl-4-(m-chloro-phenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4-dimethyl-4-(m-flourophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

EXAMPLE 5

3α-Benzoyloxy-5α-hydroxy-2β-[(3S)-3-hydroxy-trans-1-octenyl]-1α-cyclopentaneacetic acid γ lactone (Formula XXIII: $R_3$ and $R_4$ of the $L_1$ moiety are hydrogen, $R_5$ and $R_6$ of the $M_5$ moiety are hydrogen, $R_7$ is n-pentyl, $R_{16}$ is benzoyloxy, and Y is trans-CH=CH-) or its (3R)-hydroxy epimer.

Sodium borohydride (2.86 g.) is slowly added to a stirred suspension of 12.6 g. of anhydrous zinc chloride in 78 ml. of dimethyl ether in ethylene glycol (glyme) with ice bath cooling. The mixture is stirred for 20 hr. at ambient temperature and thereafter cooled to −20° C. A solution of 8.0 g. of 3α-benzoyloxy-5α-hydroxy-2β-(3-oxo-cis-1-octenyl)-1α-cyclopentaneacetic acid γ lactone (prepared according to Example 4) in 80 ml. of glyme is added over a period of 15 min. Stirring is continued for 24 hour at −20° C. and thereafter 60 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield an oil, which when chromatographed on 900 g. of silica gel packed in one percent acetone and methylene chloride, eluting with one to 15 percent acetone in methylene chloride yields the epimerically pure title product.

Following the procedure of Example 5, but using in place of the 3α-benzoyloxy-5α-hydroxy-2β-(3-oxo-trans-1-octenyl)-1α-cyclopentaneacetic acid γ lactone starting material employed therein, the various 3α-benzoyloxy-5α-hydroxy-2β-(3-oxo-trans-1-alkenyl) or substituted alkenyl-1α-cyclopentaneacetic acid γ lactones there are prepared the corresponding 3R or 3S hydroxy products.

Following the procedure of Example 5, but using in place of the 3α-benzoyloxy-5α-hydroxy-2β-(3-oxo-trans-1-octenyl)-1α-cyclopentaneacetic acid γ lactone used therein, 5α-hydroxy-2β-(3-oxo-trans-1-alkenyl or substituted alkenyl)-1α-cyclopentaneacetic acid γ lactones described following Example 4, there are prepared the corresponding 3R or 3S-hydroxy products.

For example, there are obtained the above 3α-benzoyloxy-5α-hydroxy- or 5α-hydroxy-1α-cyclopentaneacetic acid γ lactones wherein the 2β-side chain in either the 3R or 3S form consists of 3-hydroxy-trans-1-hexenyl; 3-hydroxy-trans-1-heptenyl; 3-hydroxy-trans-1-nonenyl; 3-hydroxy-trans-1-decenyl; 3-hydroxy-4-methyl-trans-1-octenyl; 3-hydroxy-4,4-dimethyl-trans-1-octenyl; 3-hydroxy-4-fluoro-trans-1-octenyl; 3-hydroxy-4,4-difluoro-trans-1-octenyl; 3-hydroxy-5-phenyl-trans-1-pentenyl; 3-hydroxy-5-(p-fluorophenyl)-trans-1-pentenyl; 3-hydroxy-5-(m-chlorophenyl)-trans-1-pentenyl; 3-hydroxy-5-(m-trifluoromethylphenyl)-trans-1-pentenyl; 3-hydroxy-4,4-dimethyl-5-phenyl-trans-1-pentenyl; 3-hydroxy-4,4-dimethyl-5-(p-fluorophenyl)-trans-1-pentenyl; 3-hydroxy-4,4-dimethyl-5-(m-chlorophenyl)-trans-1-pentenyl; 3-hydroxy-4,4-dimethyl-5-(m-trifluoromethylphenyl)-trans-1-pentenyl; 3-hydroxy-4,4-difluoro-5-phenyl-trans-1-pentenyl; 3-hydroxy-4,4-difluoro-5-(p-fluorophenyl)-trans-1-pentenyl; 3-hydroxy-4,4-difluoro-5-(m-chlorophenyl)-trans-1-pentenyl; 3-hydroxy-4,4-difluoro-5-(m-trifluoromethylphenyl)-trans-1-pentenyl; 3-hydroxy-4-phenoxy-trans-1-butenyl; 3-hydroxy-4-(p-fluorophenoxy)-trans-1-butenyl; 3-hydroxy-4-(m-chlorophenoxy)-trans-1-butenyl; 3-hydroxy-4-(m-trifluoromethylphenoxy)-trans-1-butenyl; 3-hydroxy-4,4-dimethyl-4-phenoxy-trans-1-butenyl; 3-hydroxy-4,4-dimethyl-4-(p-fluorophenoxy)-trans-1-butenyl; 3-hydroxy-4,4-dimethyl-4-(p-fluorophenoxy)-trans-1-butenyl; 3-hydroxy-4,4-dimethyl-4-(m-chlorophenoxy)-trans-1-butenyl; 3-hydroxy-4,4-dimethyl-4-(m-trifluoromethylphenoxy)-trans-1-butenyl; and the like.

EXAMPLE 6

3α-Benzoyloxy-5α-hydroxy-2β-[(3R)-3-hydroxy-3-methyl-trans-1-octenyl]-1α-cyclopentaneacetic acid γ lactone.

Refer to Chart A.

A solution of 18 g. of 3α-benzoyloxy-5α-hydroxy-2β-(3-oxo-trans-1-octenyl)-1α-cyclopentaneacetic acid γ lactone in 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hr. at 20°–25° C. then cooled to 10° C. Thereupon 370 ml. of saturated ammonium chloride is slowly added at such a rate so as to maintain the reaction mixture at ambient temperature. After 0.5 hr. the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield an oil, which is chromatographed on one kg. of silica gel packed in 10 percent ethyl acetate and Skellysolve B. Elution with 10 to 16 percent ethyl acetate in Skellysolve B (18 l.), 28 percent ethyl acetate in Skellysolve B (8 l.) yields title compound. Fractions as shown by thin layer chromatography to contain pure product are combined. Rechromatography, in the fashion described above, yields (3R)- or (3S)-epimers.

Omitting the chromatographic separation described above, the (3RS)-epimeric mixture obtained on trimethylaluminum alkylation are separated in high yield as prostaglandin-type products.

Following the procedure of Example 6, but using in place of the 3-oxo lactone starting material therein, the various lactones described following Example 4, there are obtained 3-hydroxy-3-methyl products corresponding to each of the 3-hydroxy products of Example 5.

EXAMPLE 7

3α,5α-Dihydroxy-2β[(3S)-3-hydroxy-trans-1-octenyl]-1α-cyclopentaneacetaldehyde, γ lactol, bis-(tetrahydropyranyl ether) (Formula XXVI: $R_3$ and $R_4$ of the $L_1$ moiety are hydrogen, $M_6$ is

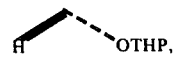

$R_7$ is n-butyl, $R_{18}$ is tetrahydropyran-2-yloxy, and Y is trans-CH=CH-) or its (3R) epimer.

Refer to Chart A.

A. A solution of 5 g. of the reaction product of Example 5 in 150 ml. of methanol is purged with nitrogen. Thereafter, potassium carbonate (2.02 g.) is added and the resulting mixture is stirred at ambient temperature until thin layer chromatographic analysis shows the solvolysis to be complete (about 1.5 hr.). The methanol is then evaporated under reduced pressure. The residue

67 is then shaken with ethyl acetate (250 ml.), brine (250 ml.), and 8 g. of potassium bisulfate. The aqueous layer is then extracted twice with 125 ml. of ethyl acetate and the organic extracts are dried over magnesium sulfate, and evaporated to yield an oil. This oil is then dissolved in chloroform and a few crystals of p-toluenesulfonic acid are added. When thin layer chromatography indicates the action is complete (about 2 hr.), the reaction mixture is then washed with aqueous potassium bicarbonate, dried, and evaporated to yield an oil which is then chromatographed using silica gel packed in one percent ethanol in methylene chloride for purification. Accordingly, the formula XXIV deacylated lactone is prepared.

B. A solution of 1.57 g. of the reaction product of part A above, in 35 ml. of methylene chloride (containing 2.5 ml. of dihydropyran and 100 mg. of pyridine hydrochloride) is allowed to stand for 23 hr. at ambient temperature. The reaction mixture is then washed with water, aqueous potassium bicarbonate, dried over magnesium sulfate, and evaporated, yielding an oil which is thereafter chromatographed on 200 g. of silica gel packed in one percent acetone in methylene chloride. Elution with from one to ten percent acetone in methylene chloride yields the formula XXV bis-tetrahydropyranyl lactone corresponding to the lactone reaction product of part A above.

C. A solution of the reaction product of part B above in 20 ml. of toluene is cooled to −70° C. and thereafter 10 ml. of 10 percent diisobutylaluminum hydride in toluene is slowly added. The reaction mixture is then stirred at −70° C. until thin layer chromatographic analysis indicates that the reaction is complete (about 30 min.). Thereafter the cooling bath is removed and 9 ml. of a mixture of tetrahydrofuran and water (2:1) is added slowly. The reaction mixture is then stirred and allowed to warm to room temperature, and is then filtered through Celite. The filter cake is rinsed with benzene, combined organic extracts are then dried over magnesium sulfate and evaporated to yield the title compound.

Following the procedure of Example 7, but using as starting material 3α-benzoyloxy-5α-hydroxy-2β-[(3R) or (3S)-3-hydroxy-3-methyl-trans-1-octenyl]-1α-cyclopentaneacetic acid γ lactone, there is obtained the corresponding bis-tetrahydropyranyl ether lactol.

Following the procedure of Example 7, the 3α-benzoyloxy-5-hydroxy or 5-hydroxy lactones described in and following Example 5 or 6 are transformed into corresponding lactols.

Following the procedure of Example 5, but using the title compound of Example 4 as starting material, there is prepared 3α-benzoyloxy-5α-hydroxy-2β-[(3S)-4,4-difluoro-3-hydroxy-trans-1-octenyl]-1α-cyclopentaneacetic acid γ lactone or its (3R) epimer.

Following the procedure of Example 7, there is prepared 3α,5α-dihydroxy-2β-[(3R)-3-hydroxy-4,4-difluoro-trans-1-octenyl]-1α-cyclopentaneacetaldehyde γ lactol, bis-tetrahydropyranyl ether from the corresponding acylated lactone.

Following the procedure of Example 7, but using any of the lactones described following Examples 5 or 6, there are prepared the corresponding δ-lactols.

EXAMPLE 8

3α,5α-Dihydroxy-2β-[(3S)-3-hydroxy-trans-1-octenyl-1α-cyclopentanepropionaldehyde δ-lactol bis tetrahydropyranyl ether) (Formula XXXII: n is 2, R$_3$ and R$_4$ of the L$_1$ moiety are hydrogen, M$_6$ is

R$_7$ is n-butyl, R$_{18}$ is tetrahydropyranyloxy, and Y is trans-CH=CH-).

Refer to Chart A.

A. A suspension of methoxymethyltriphenylphosphonium chloride (32.4 g.) in 150 ml. of tetrahydrofuran is cooled to −15° C. To the suspension is added 69.4 ml. of n-butyllithium in hexane (1.6 molar) in 45 ml. of tetrahydrofuran. After 30 min. There is added a solution of 3α,5α-dihydroxy-2β-[(3S)-3-hydroxy-trans-1-octenyl]-1α-cyclopentaneacetaldehyde γ lactol bis-(tetrahydropyranyl)ether, Example 7 (10 g.), in 90 ml. of tetrahydrofuran. The mixture is stirred for 1.5 hr. while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVII product are combined.

B. The reaction product of part A above in 20 ml. of tetrahydrofuran is hydrolyzed with 50 ml. of 66 percent aqueous acetic acid at about 57° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The title compound is thereby obtained by combining and concentrating fractions as shown by thin layer chromatography to contain pure product. Accordingly, there is obtained the corresponding formula XXVIII δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol, 9:1), silver oxide is removed by filtration. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula XXIX lactone.

D. The formula XXIX lactone prepared in part C above is then transformed to its bis-tetrahydropyranyl ether derivative following the procedure described in Example 7, part B.

E. The formula XXX compound prepared in part D above is then reduced to the corresponding title δ lactol bis-tetrahydropyranyl ether by the procedure described in Example 7, part C.

Following the procedure of Example 8, but using the corresponding (3R) starting material in place of the (3S) starting material there is obtained the corresponding (3R)-lactol product.

Following the procedure of Example 8, but using the place of the formula XXVI lactol, the various formula XXVI lactols described following Example 7, there are obtained the corresponding formula XXXII lactols wherein $n$ is 2.

EXAMPLE 9 cis-4,5-Didehydro-PGF$_1$, 11,15-bis-(tetrahydropyranyl) ether (Formula XXXIII: $n$ is 2, $g$ is one, $R_2$ and $R_3$ and $R_4$ of the $L_1$ moiety are hydrogen, $M_6$ is

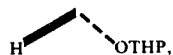

$R_1$ is hydrogen, $R_7$ is n-butyl, $R_{18}$ is tetrahydropyranyloxy, and Y is trans-CH=CH-) or its 15-epimer.

Refer to Chart A.

3-Carboxypropyltriphenylphosphonium bromide (prepared by heating 4-bromobutyric acid and triphenylphosphine in benzene at reflux for 18 hr., and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula XXXII lactol of Example 8 and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield pure product.

Following the procedure of Example 9, but using in place of the (3S) starting material the corresponding (3R) starting material there is obtained the corresponding 15-epi-cis-4,5-didehydro-PGF$_1$ -type compound.

Following the procedure of Example 9, but using in place of the 3-carboxypropyltriphenylphosphonium bromide, 4-carboxybutyltriphenylphosphonium bromide, or 5-carboxypentyltriphenylphosphonium bromide, there are prepared the corresponding formula XXXIII compounds wherein $g$ is 2 or 3.

Further, following the procedure of Example 9, but using in place of the formula XXXII starting material the various formula XXXII δ-lactols described following Example 8, there are prepared the corresponding cis-4,5-didehydro-PGF$_1$ or 11-deoxy-PGF$_1$ -type bis (tetrahydropyranyl ethers).

Likewise using the formula XXXII γ-lactols, there are prepared the formula XXXIII PGF$_2$ -or 11-deoxy-PGF$_2$ -type compounds wherein $n$ is one and $g$ is one, 2, or 3 when 4-carboxybutyl-, 5-carboxypentyl, or 6-carboxyhexyltriphenylphosphonium bromide are used respectively. Further, the corresponding ω,ω-difluoro-ω-carboxyalkyl-triphenylphosphonium bromides yield corresponding 2,2-difluoro-PGF$_2$ -type THP ethers.

EXAMPLE 10

2,2-Difluoro-16-phenoxy-17,18,19,20-tetranor-PGF$_2$ , methyl ester, 11,15-bis-tetrahydropyranyl ether (Formula XXXII: $g$ is one, $R_2$ is fluoro, $R_3$ and $R_4$ of the $L_1$ moiety are hydrogen, $M_6$ is

$R_1$ is methyl, $R_7$ is phenoxy, $R_{18}$ is tetrahydropyranyloxy, and Y is trans-CH=CH-) or its 15-epimer.

Refer to Chart A.

A. Sodium hydride (0.57 g., 57 percent in mineral oil) in 25 ml. of dimethylsulfoxide, is added to 3 g. of 4,4-difluoro4-carboxybutyltriphenylphosphonium bromide. The reaction mixture is maintained at 20° C. with stirring for 30 min. A solution of 3α,5α-dihydroxy-2β-[(3R)-3-hydroxy-4-phenoxytrans-1-butenyl]-1α-cyclopentaneacetaldehyde γ-lactol bis(tetrahydropyranyl ether), 1.57 g., in 10 ml. of dimethylsulfoxide is added. The reaction mixture is stirred at ambient temperature for 2 hr. and diluted with 50 ml. of benzene. Potassium bisulfate (2.7 g. in 30 ml. of water) is slowly added, maintaining the reaction temperature at less than or equal to 10° C. The aqueous layer is extracted with 50 ml. of benzene and the organic extracts are washed successively with 50 ml. of water and 50 ml. of brine before combining, drying, and evaporating. Evaporation yields an oil which is chromatographed on 100 g. of acid washed silica gel packed in 20 percent ethyl acetate and Skellysolve B. Elution with 20–75 percent ethyl acetate and Skellysolve B yields crude 2,2-difluoro-16-phenoxy-17,18,19,20-tetranor-PGF$_2$ , bis-(tetrahydropyranyl ether).

B. A solution of the crude reaction product of part A above and 15 ml. of diethyl ether is esterified with diazomethane, used in stoichiometric excess. The crude methyl ester is chromatographed on 100 g. silica gel packed in 2 percent acetone methylene chloride. Elution with 2–12 percent acetone in methylene chloride yields the title compound.

Following the procedure of Example 10, but using the (3S) lactol there is obtained the corresponding 15-epiPGF$_2$ , methyl ester, 11,15-bis-tetrahydropyranyl ether.

Following the procedure of Example 10, but using 5,5-difluoro-5-carboxypentyltriphenylphosphonium bromide or 6,6-difluoro-6-carboxyhexyltriphenylphosphonium bromide in place of 4-carboxybutyltriphenylphosphonium bromide there is obtained the corresponding 2a-homo or 2a,2b-di-homo-2,2-difluoro-PGF$_2$ -type compound of its 15-epimer,

EXAMPLE 11 cis-4,5-Didehydro-15-methyl-17-phenyl-18,19,20-trinor-11-deoxy-PGF$_1$ , methyl ester (Formula XXXIX: $R_3$ and $R_4$ of the $L_1$ moiety are hydrogen, $M_1$ is

$Z_2$ is cis-$CH_2$-CH=CH-$(CH_2)_2$-, $M_{19}$ is

$R_1$ is methyl, $R_7$ is benzyl, $R_8$ is hydrogen, Y is trans-CH=CH-,) or its 15-epimer.

A. A solution of 5.7 g. of 5α-hydroxy-2β-[(3S)-3-hydroxy-3-methyl-5-phenyl-trans-1-pentenyl]-1α-cyclopentaneacetic acid δ lactone in 150 m. of tetrahydrofuran is cooled to −60° C. Diisobutylaluminum hydride and toluene (85 ml.) is added over a period of 23 min. at a temperature of −70° C. The reaction mixture is stirred for an additional 24 min. Thereafter 100 ml. of saturated aqueous ammonium chloride solution is slowly added at a temperature of −60° C. The resulting mixture is then stirred and allowed to warm to room temperature, yielding a gel as precipitate. This mixture is then diluted with 70 ml. of water and 150 ml. of ethyl acetate, mixed thoroughly and filtered. The filter cake is washed with water and ethyl acetate. the aqueous layer is extracted with ethyl acetate. The combined organic extracts are washed with brine, dried over sodium sulfate, and evaporated to yield a lactol corresponding to lactone starting material as a cloudy oil.

B. Following the procedure of Example 10, sodium hydride in dimethylsulfoxide is combined with 3-carboxypropyltriphenylphosphonium bromide to yield the title compound in free acid form.

The reaction product of part B above is esterified with diazomethane following the procedure described above, and chromatographed yielding the title compound.

EXAMPLE 12 cis-4,5-didehydro-15-methyl-17-phenyl-18,19,20-trinor-11-deoxy-PFG$_1$

A solution of 2.0 g. of the reaction product of Example 11, or its 15-epimer, in 20 ml. of methanol is cooled to 0° C. The resulting mixture is thereafter treated dropwise under a nitrogen atmosphere with 12 ml. of 10 percent aqueous sodium hydroxide solution. The mixture is then allowed to warm to room temperature and stirred for 2 hr. After removal of the methanol by evaporation under reduced pressure the residue is diluted with water and extracted with methylene chloride. The aqueous layer is then cooled with ice, treated with 24 ml. of 2 molar aqueous sodium bisulfate solution and extracted immediately with ethyl acetate. The combined organic extracts are washed with brine, dried over anhydrous sodium sulfate, and concentrated. Crude product may then be chromatographed on 150 g. of acid-washed silica gel, yielding the title compound or its 15-epimer.

Following the procedure of Example 15, but using any of the methyl esters described above there are prepared the corresponding free acid compounds.

EXAMPLE 13

2,2-Difluoro-16-phenoxy-17,18,19,20-tetranor-PFG$_2$ or its 15-epimer.

2,2-Difluoro-16-phenoxy-17,18,19,20-tetranor-PFG$_2$ -bis(tetrahydropyranyl ether) (0.60 g.) is reacted with 30 ml. of tetrahydrofuran, water, and acetic acid (1:3:6) at 40° C. for 4 hr. Thereafter, the resulting mixture is diluted with 60 ml. of water and freeze dried. The residue is then extracted with diethyl ether and washed with brine. The diethyl ether extract is then dried using magnesium sulfate and evaporated to yield product which is chromatographed to yield pure product.

EXAMPLE 14

5-Oxa-PFG$_1$, methyl ester, 11,15-bis-(tetrahydropyranyl) ether (Formula XXXVI: g is one, $R_3$ and $R_4$ of the $L_1$ moiety are hydrogen, $M_6$ is

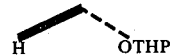

$R_1$ is methyl, $R_7$ is n-butyl, $R_{18}$ is tetrahydropyranyloxy, and Y is trans-CH=CH-) or its 15-epimer.

Refer to Chart A.

A. A mixture of the title product of Example 7 (6.3 g.) and 50 ml. of 95 percent ethanol is treated at 0° C. with stirring with a solution of sodium borohydride in 10 ml. of water (added over a period of one min.). The resulting mixture is then stirred at 0° C. for 10 min. and then shaken with 10 ml. of water, 250 ml. of ethyl acetate, and 150 ml. of brine. The organic phase is then washed with brine, dried, and concentrated under reduced pressure to yield 2-decarboxy-2-hydroxymethyl-2,3,4,5,6-pentanor-PFG$_1$, 11,15-bis-tetrahydropyranyl ether.

B. A solution of potassium tert-butoxide (1.77 g.) in 30 ml. of tetrahydrofuran is mixed at 0° C., with stirring, with a solution of the reaction product of part A (5.8 g.) in 30 ml. of tetrahydrofuran. The resulting mixture is then stirred at 0° C. for 5 min. and thereafter 5 ml. of trimethyl ortho-4-bromobutyrate is added. Stirring is continued at 0° C. for 2 hr. and at about 25° C. for 16 hr. To this mixture is added 30 ml. of dimethylformamide and 0.5 g. of potassium-t-butoxide. The resulting mixture is then stirred for 20 hr. Some of the solvent is then removed under reduced pressure and the residue is then shaken with water and diethylether and dichloro methane (3:1). The organic phase is then washed with water and brine, dried, and concentrated. The residue, containing the ortho ester, is dissolved in 60 ml. of methanol at 0° C. and treated with 15 ml. of cold water containing 2 drops of concentrated hydrochloric acid. The mixture is stirred at 0° C. for 5 min. and shaken with 200 ml. of diethyl ether, 50 ml. of dichloromethane, and 200 ml. of brine. The organic phase is washed with brine, dried, concentrated under reduced pressure, and the residue chromatographed, yielding title product.

EXAMPLE 15

3-Oxa-3,7-inter-m-phenylene-4,5,6-trinor-PGF$_1$ (Formula LXXIII: $R_1$ is hydrogen, $R_3$ and $R_4$ of the $L_1$ moiety and $R_5$ and $R_6$ of the $M_1$ moiety are all hydrogen, $R_7$ is n-butyl, and g is one) or 3,7-inter-m-phenylene4,5,6-trinor-PGF$_1$ (Formula LXXXIV: g is one, $R_1$ is hydrogen, $R_3$ and $R_4$ of the $L_1$ moiety and $R_3$ and $R_6$ of the $M_1$ moiety are all hydrogen, $R_7$ is n-butyl, $Z_3$ is —O—).

Refer to Charts B, C, and D.

A. Optically Active Bicyclo[3.1.0]-hex-2-ene-6-endocarboxaldehyde.

Following the procedure of Preparation 1 of U.S. Pat. No. 3,711,515, racemic bicyclo[3.1.0]hex-2-ene-6- endo-carboxaldehyde is prepared from bicyclo[2.2.1-]hepta2,5-diene and peracetic acid.

The racemic compound is resolved by the procedure of Example 13 of U.S. Pat. No. 3,711,515, forming an oxazolidine as follows:

Racemic bicyclo[3.1.0]hex-2-ene-6-endo-carboxyaldehyde (12.3 g.) and 1-ephedrine (16.5 g.) are dissolved in about 150 ml. of benzene. The benzene is removed under vacuum and the residue taken up in about 150 ml. of isopropyl ether. The solution is filtered, then cooled to −13° C. to yield crystals of 2-endo-bicyclo-[3.1.0]hex-2-en-6-yl-3,4-dimethyl-5-phenyl-oxazolidine, 11.1 g., m.p. 90°–92° C. Three recrystallizations from isopropyl ether, cooling each time to about −2° C., yield crystals of the oxazolidine, 2.2 g., m.p. 100°–103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatograph-grade (Merck), 0.05–0.2 mm. particle size, with about 4–5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are (λ in nm., θ): 350, 0; 322.5, 4,854; 312, -5,683; 302.5, -4,854; 269, 0; 250, 2,368; 240, 0; and 210, -34,600.

B. 1-bicyclo[3.1.0]hex-2-ene-6-endo-carboxaldehyde Neopentyl Glycol Acetal (Formula LXI: $R_{55}$ and $R_{56}$ taken together are :$CH_2$-$C(CH_3)_2$-$CH_2$- and ~ is endo).

A mixture of 2,2-dimethyl-1,3-propanediol (900 g.), 5 1. of benzene, and 3 ml. of 85 percent phosphoric acid is heated at reflux. To it is added, in 1.5 hr., a solution of optically active bicyclo[3.1.0]hex-2-ene-6-endocarboxaldehyde (part A, 500 g.) in one liter of benzene. Provision is made to take off azeotropically distilled water with a Dean-Stark trap. After 3 hr. the mixture is cooled and extracted with 2 liters of 5 percent sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to −13° C. to yield 300 g. of the title compound, m.p. 52°–55° C., and and having NMR peaks at 0.66, 1.20, 0.83–2.65, 3.17–3.8, 3.96, and 5.47–5.88 δ, [α]$_D$−227° (C=0.8967 in methanol), and $R_f$ 0.60 (TLC on silica gel in 25 percent ethyl acetate in mixed isomeric hexanes). Further work-up of the mother liquors yields 50–100 g. of additional product.

C. d-8-(m-Acetoxyphenyl)-7-oxa-tricyclo-[4.2.0.0$^{2,4}$]-octane-6-endo-carboxaldehyde Neopentyl Glycol Acetal (Formula LXII: $R_{55}$ and $R_{56}$ taken together are —$CH_2$-$C(CH_3)_2$—$CH_2$-, $R_{63}$ is

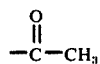

and ~ is endo).

A solution of the formula LXI 1-bicyclo[3.1.0]hex-2-ene-6-endo-carboxaldehyde neopentyl glycol acetal (Part B, 5.82 g.) and m-acetoxy-benzaldehyde (1.64 g.) in 25 ml. of benzene is charged to a Pyrex photolysis vessel equipped with an immersible water-cooled coldfinger and a fritted gas inlet tube. Dissolved oxygen is removed by bubbling nitrogen through the solution. The mixture is then irradiated at 350 nm. with a Rayonet Type RS Preparative Photochemical Reactor (The Southern New England Ultraviolet Co., Middletown, Conn.) equipped with six RUL 3500 A lamps. After 24 hr. the photolysate is concentrated under reduced pressure to a pale yellow oil, 10 g., which is subjected to silica gel chromatography. Elution with 10–70 percent ethyl acetate in Skellysolve B (mixture of isomeric hexanes) yields separate fractions of the recovered starting materials and the formula LXII title compound, a pale yellow oil, 0.86 g., having NMR peaks at 0.68, 1.20, 0.8–2.5, 2.28, 2.99, 3.12–3.88, 3.48, 4.97–5.52, and 6.78–7.60 δ; infrared absorption bands at 3040, 2950, 2860, 2840, 1765, 1610, 1590, 1485, 1470, 1370, 1205, 1115, 1020, 1005, 990, 790, and 700 cm.$^{-1}$; mass spectral peaks at 358, 357, 116, 115, 108, 107, 79, 70, 69, 45, 43, and 41; [α]$_D$ +55° (C=0.7505 in 95 percent ethanol); and $R_f$ 0.18 (TLC on silica gel in 25 percent ethyl acetate in mixed isomeric hexanes).

D. d-2-Exo-[m-(pivaloyloxy)benzyl]-3-exo-pivaloyloxy)-bicyclo-[3.1.0]hexane-6-endo-carboxaldehyde Neopentyl Glycol Acetal (Formula LXIV: $R_{55}$ and $R_{56}$ taken together are-$CH_2$-$C(CH_3)_2$-$CH_2$-, $R_{68}$ is

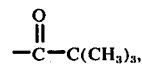

and ~ is endo).

A mixture os lithium (0.25 g.) in 70 ml. of ethylamine is prepared at 0° C. and cooled to −78° C. A solution of the formula LXII d-8-(m-acetoxyphenyl)-7-oxa-tricyclo[4.2.0.0$^{2,4}$]-octane-6-endo-carboxaldehyde neopentyl glycol acetal (part C 1.83 g.) in 10 ml. of tetrahydrofuran is added dropwise in about 5 min. After stirring at −78° C. for about 3.5 hr. the reaction is quenched with solid ammonium chloride and water-tetrahydrofuran. The mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine and saturated aqueous sodium bicarbonate (1:1), and dried over sodium sulfate. Concentration under reduced pressure yields the formula LXIII diol as a pale tan oil, 1.64 g., having $R_f$ 0.03 (TLC on silica gel in 25 percent ethyl acetate in mixed isomeric hexanes).

The product of the proceeding paragraph is dissolved in 30 ml. of pyridine and treated with 1.5 ml. of pivaloyl chloride over a period of 22 hr. at about 25° C. The reaction mixture is mixed with water, then brine and extracted with ethyl acetate. The organic phase is washed successively with brine, water, saturated aqueous copper (11) sulfate, saturaged aqueous sodium bicarbonate, and brine, and dried over sodium sulfate. Concentration under reduced pressure yields a residue, 2.53 g., which is subjected to silica gel chromatography to yield the formula LXIV title compound, 1.87 g., having NMR peaks at 0.71, 1.20, 1.33, 0.9–3.1, 3.28–4.00, 4.17, 4.7–5.2, and 6.77–7.53 δ; mass spectral peaks at 486, 485, 115, 73, 72, 57, 44, 43, 42, 41, 30, 29, 15; [α]$_D$ +19°(C=0.9340 in ethanol); and $R_f$ 0.50 (TLC on silica gel in 25 percent ethyl acetate in mixed isomeric hexanes).

E. 2-Exo-[m-(pivaloyloxy)benzyl]-3-exo-(pivaloyloxy)bicyclo[3.1.0]hexane-6-endo-carboxaldehyde (Formula LXV: $R_{66}$ is

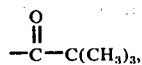

and ~ is endo).

The formula LXIV acetal, i.e. d-2-exo-(m-pivaloyloxy)-benzyl]-3-exo-(pivaloyloxy)-bicyclo[3.1.0]hexane-6-endocarboxaldehyde neopentyl glycol acetal (part D, 0.48 g.) is treated at 0° C. with 25 ml. of 88 percent formic acid for 4 hr. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromatography. Elution with 5–15 percent ethyl acetate in Skellysolve B yields the formula LXV title compound as an oil, 0.37., having NMR peaks at 1.20, 1.33, 0.6–3.2, 5.1–5.5, 6.6–7.5, and 9.73 $\delta$; and $R_f$ 0.50 (TLC on silica gel in 25 percent ethyl acetate in mixed isomeric hexanes).

F. 2-Exo-[m-(pivaloyloxy)benzyl]-3-exo-(pivaloyloxy)-6-endo-(cis-1-heptenyl)-bicyclo[3.1.0-]hexane (Formula LXVI: $R_3$ and $R_4$ of the $L_1$ moiety are both hydrogen, $R_7$ is n-butyl, $R_{66}$ is

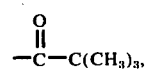

$R_{53}$ is hydrogen, and ~ is endo); and 2-Exo-(m-hydroxy-benzyl)-3-exo-hydroxy-6-endo-(cis-1-heptenyl)bicyclo[3.1.0]-hexane (Formula LXVII: $R_3$ and $R_4$ of the $L_1$ moiety are both hydrogen, $R_7$ is n-butyl, $R_{53}$ and $R_{66}$ are hydrogen, and ~ is endo).

A Wittig ylid reagent is prepared in 10 ml. of benzene from n-hexyltriphenylphosphoniumbromide (0.79 g.) and nbutyllithium (0.6 ml. of 2.32 M. solution in hexane) at about 25° C. for 0.5 hr. After the precipitated lithium bromide has settled, the solution is removed and added to a cold (0° C.) slurry the formula LXV aldehyde (part E, 0.37 g.). After 15 min. there is added 1.0 ml. of acetone and the mixture is heated to 60° C. for 10 min. The mixture is concentrated under reduced pressure. The residue is washed with 10 percent ethyl acetate in Skellysolve B and these washings are concentrated to the formula LXVI title compound, an oil, 0.33 g. having NMR peaks at 1.18, 1.33, 0.6–3.2, 4.5–6.0, and 6.67–7.62 $\delta$; and $R_f$ 0.78 (TLC on silica gel in 25 percent ethyl acetate in Skellysolve B).

The above product of the preceding paragraph is transformed to the formula LXVII diol by treatment with sodium methoxide (2.5 ml. of a 25 percent solution in methanol) for 4 hrs., followed by addition of 0.5 g. of solid sodium methoxide and further stirring for 15 hr. at 25° C., then at reflux for 6 hr. The mixture is cooled, mixed with 300 ml. of brine, and extracted with ethyl acetate. The organic phase is washed with brine, dried over magnesium sulfate, and concentrated under reduced pressure to a residue, 0.27 g. the residue is subjected to silica gel chromatography, eluting with 25–35 percent ethyl acetate in Skellysolve B, to yield the formula-LXVII title compound as an oil, 0.21 g., having NMR peaks at 0.87, 0.6–3.25, 3.88–4.35, 4.82–5.92, and 6.47–7.33 $\delta$; and $R_f$ 0.13 (TLC on silica gel in 25 percent ethyl acetate in Skellysolve B).

B. 2-Exo- m-[(carboxy)methoxy]benzyl -3-exo-hydroxy-6-endo-(cis-1-heptenyl)bicyclo[3.1.0]hexane (Formula LXVIII: $R_3$ and $R_4$ of the $L_1$ moiety are both hydrogen, g is one, $R_7$ is n-butyl, $R_1$, $R_{53}$ and $R_{66}$ are hydrogen, and ~ is endo).

The formula-LXVII diol, i.e. 2-exo(m-hydroxybenzyl)-3-exo-hydroxy-6-endo-(cis-1-heptenyl)bicyclo[3.1.0]hexane (part F, 0.19 g.) is treated in 8 ml. of dioxane with bromoacetic acid (0.61 g.) and 6 ml. of 1N aqueous sodium hydroxide. After the mixture has been heated at reflux for 3 hr., with sodium hydroxide solution added when necessary to maintain a pH of about 10, the mixture is cooled, diluted with 100 ml. of water, and extracted with diethyl ether. The aqueous phase is acidified to pH 1–2 and extracted with ethyl acetate to yield the formula-LXVIII title compound, a pale yellow oil, 0.20 g. Recovered formula LXVIII diol is obtained from the diethyl ether organic phase on drying and concentrating, 0.025 g.

H. 3-Oxa-3,7-inter-m-phenylene-4,5,6-trinor-PGF$_1$ (Formula LXXIII: $R_3$ and $R_4$ of the $L_1$ moiety and $R_5$ and $R_6$ of the $L_1$ moiety are all hydrogen, $R_7$ is n-butyl, g is one, and $R_1$ is hydrogen).

The formula LXVIII alkene is transformed to the title compound applying the procedures disclosed in U.S. Pat. No. 3,711,515. Thus, compound LXVIII (part G) is hydroxylated by the procedures of Example 6 of that patent to the formula LXIX glycol of Chart B, uisng osmium tetroxide either alone or in combination with N-methylmorpholine oxide-hydrogen peroxide complex.

The glycol is then either (1) sulfonated, for example to yield the bismesylate, and then hydrolyzed to a mixture of the title compound and its 15-epimer, applying the procedures of Example 7 of that patent, or (2) treated with substantially 100 percent formic acid to form the diformate of LXIX and thereafter hydrolyzed to a mixture of the title compound and its 15 epimer, applying the procedures of Examples 20 and 21 of that patent. The epimers are separated by silica gel chromatography to yield the title compound and its 15-epimer.

A third route from glycol LXIX to compound LXXIII is by way of a cyclic ortho ester

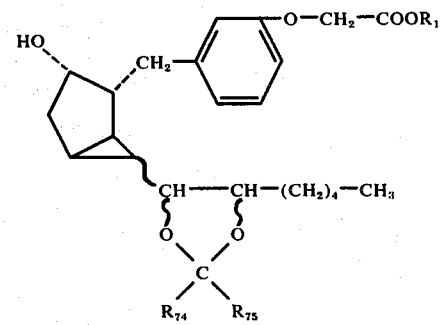

wherein $R_{74}$, $R_{75}$, and ~ are as defined above. The glycol is treated as a 1–20 percent solution in benzene with trimethyl orthoformate (1.5–10 molar equivalents) and a catalytic amount (1 percent of the weight of the glycol) of pyridine hydrochloride at about 25° C. The reaction is followed by TLC (thin layer chromatography) and is complete in a few minutes. There is thus obtained the cyclic ortho ester in 100 percent yield.

The cyclic ester is then treated with 20 volumes of 100 percent formic acid at about 25° C. In about 10 min. the reaction mixture is quenched in water or aqueous alkaline bicarbonate solution and extracted with dichloromethane. The organic phase is shaken with 5 percent aqueous sodium bicarbonate, dried over sodium sulfate, and concentrated to yield the corresponding diester. The diester is contacted with 10–50 volumes of anhydrous methanol and 10–20 percent of its weight of potassium carbonate at about 25° C. until the ester groups are removed. The mixture of 15-epimers thus obtained is then separated to yield the formula LXXIII compound or its 15-epimer.

i 2-Exo-[m-(2-carboxyethyl)benzyl]-3-exo-hydroxy-6-endo(cis-1-heptenyl)bicyclo-[3.1.0]hexane (Formula LXXXII, $Z_3$ is methylene, g is one, $R_3$ and $R_4$ of the $L_1$ moiety are hydrogen, $R_7$ is n-butyl, $R_1$ and $R_{53}$ are hydrogen and ~ is endo).

With respect to Chart C, there is first prepared the formula LXXVI oxetane. Following the procedures of part C, but replacing the m-acetoxybenzaldehyde of part C with the aldehyde of the formula

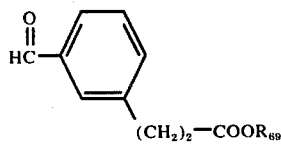

wherein $R_{69}$ is as defined above, the corresponding formula LXXVII oxetanes are obtained with a fully developed side chain.

Thereafter, following the procedures of parts D, E, and F, but replacing the formula LXII oxetane of part D with the oxetane obtained by the procedure of the preceeding paragraph of this part, there are obtained the corresponding formula LXXXI products.

Finally, the blocking groups on each LXXXI compound are removed by methods disclosed herein or known in the art to yield the formula LXXXII compound.

J. 3,7-inter-m-phenylene-4,5,6-trinor-$PGF_1$ (Formula LXXXIV: $R_1$ is hydrogen $R_2$ and $R_3$ of the $L_1$ moiety and $R_5$ and $R_6$ of the $M_1$ moiety are hydrogen, $R_7$ is n-butyl, g is one, Y is trans-CH=CH- and $Z_3$ is -$CH_2$-).

Following the procedures of part H, the formula LXXXII alkene is transformed in several steps to the formula LXXXIV compound.

Following the procedures described in Example 15, but using various alternate intermediate and starting materials, there are prepared the various 3-oxa-3,7-inter-m-phenylene- or 3,7-inter-m-phenylene-4,5,6-trinor-$PGF_1$ -type compounds disclosed herein.

EXAMPLE 16

$PGD_2$ or $PGD_2$, methyl ester (Formula CIX). Refer to Chart E.

A. $PGF_2$ (2.0 g.) and methylene chloride (50 ml.) is treated with 688 mg. of n-butyl boronic acid. The reaction mixture is then stirred vigorously and heated to boiling, adding 5 ml. aliquots of methylene chloride to replace amounts lost through evaporation. The procedure is continued for about 25 min. adding about 20 to 25 ml. of methylene chloride. The resulting distillate becomes clear. Thereafter 10 ml. of dihydropyran is added to the reaction mixture followed by addition of pyridine hydrochloride (150 mg.). After 20 hr. at 40° C. the reaction is complete and the methylene chloride is removed under reduced pressure and the residue combined with 30 ml. of methanol and 13 ml. of a 3N aqueous potassium hydroxide solution. The resulting solution is allowed to stand for 2 hr. and thereafter treated with 5 ml. of 30 percent sodium peroxide and 30 ml. of water. The methanol is then removed under reduced pressure and the aqueous residue diluted with 100 ml. of water and extracted twice with diethyl ether. The aqueous layer is then acidified with 25 ml. of 2N aqueous potassium bisulfate and extracted with ethyl acetate. The combined organic extracts are then combined, washed with brine, and dried over anhydrous sodium sulfate. Removal of solvent under reduced pressure yields 3.3 g. of an oil which is chromatographed on 100 g. of acid washed silica gel. The column is packed with and eluted with 75 percent ethyl acetate in hexane. The formula CIV $PGF_2$ , 15-(tetrahydropyranyl ether) is thereby obtained.

B. $PGF_2$ , 15-(tetrahydropyranyl ether) (2 g.) in acetone (75 ml.) is cooled to −45° C. and thereafter treated with 1.2 ml. of the Jones reagent. The mixture is stirred for 30 min at −35 to −45° C. and thereafter treated with 0.5 ml. of isopropanol and stirred an additional 15 min. The reaction mixture is then poured into a mixture of ice, water, and diethyl ether. The mixture is then extracted with diethyl ether and the combined ethereal extracts washed with brine, and dried over sodium sulfate. After filtration removal of solvent proceeds by rotary evaporation . Crude product (1.8 g.) thereby obtained is chromatographed on 360 g. of silica gel eluting with 45 percent ethyl acetate in hexane. $PGD_2$ 15-tetrahydropyranyl ether (800 mg.) is thereby obtained.

C. $PGD_2$, 15-(tetrahydropyranyl ether) (800 mg.) in 20 ml. of acetic acid and 10 ml. of water is heated at 40° C. for 2 hr. and then diluted with 100 ml. of water and thereafter freeze dried. The residue is then chromatographed on 50 g. of acid washed silica gel packed with 20 percent ethyl acetate in hexane. Elution with 35 to 65 percent ethyl acetate in hexane yields 500 mg. of a colorless oil, which cyrstallizes on standing. The melting point is 62.8–63.3° C.

Following the procedure of Example 16, but using any of the various PGF -type compounds described herein or known in the art there are prepared the corresponding PGD-type compounds.

EXAMPLE 17

9-Deoxy-9,10-didehydro-$PGD_2$ (Formula CX: $R_1$ is hydrogen, $Z_1$ is cis-CH=CH-$(CH_2)_3$-, Y is trans-CH=CH-, $R_3$ and $R_4$ of the $L_1$ moiety and $R_5$ of the $M_1$ moiety are all hydrogen, and $R_7$ is n-butyl).

Refer to Chart E.

Quantities of $PGD_2$ are subject to silica gel chromatography until about 3.9 g. of less polar (than $PGD_2$) impurities are obtained from eluant fractions.

The 3.9 g. of less polar impurities are then chromatographed on 11.2 g. of silica gel packed with 5 percent acetone in methylene chloride eluting with 10 to 15 percent acetone in methylene chloride. Partially purified title product (1.2 g.), thereby obtained, is chromatographed on 200 g. of neutral silica gel packed with ethyl acetate, methanol, and chloroform (1:1:18). This column is washed with 800 ml. of ethyl acetate, methanol, and chloroform (1:1:48) and the above partially purified product thereafter added to the column. Eluting with ethyl acetate, methanol, and chloroform (1:1:48) pure title product.

EXAMPLE 18

9-Deoxy-PGD$_2$

Refer to Chart 1.

A. Following the procedure of Example 17, the reaction product of Example 16, part A is dehydrated to yield 9,10-didehydro-9-deoxy-PGD$_2$, 15-tetrahydropyranyl ether.

B. To a stirred solution of the reaction product of step A dissolved in methanol at −20° C. under a nitrogen atmosphere there is added a solution of sodium borohydride in water and methanol. The resulting mixture is stirred for 20 min. and thereafter acetic acid is added cautiously. The resulting mixture is then concentrated and water is added and the pH is adjusted to about 3 with the addition of citric acid. The mixture is extracted with dichloromethane and the combined organic extracts are washed with water and brine and dried and concentrated to yield a formula CXXIII compound.

C. To a solution of the reaction product of step B dissolved in acetone at −20° C., there is added dropwise with stirring over one min. the Jones reagent (chromium trioxide, water, and concentrated sulfuric acid). The resulting mixture is then stirred at −20° C. for 20 min. and thereafter isopropanol is added and the mixture is stirred at −20° C. for an additional 10 min. The mixture is then diluted with water and extracted with diethyl ether. The ethereal extracts are then washed with water and brine, dried, and concentrated. The residue is then chromatographed on silica gel yielding pure formula CXIV product.

D. The title compound is then prepared by hydrolysis of the C-15 blocking group by the procedure of Example 13.

Following the procedure of Example 17 or 18, there are prepared 9-deoxy-9,10-didehydro-PGD- or 9-deoxy-PGD-type compounds corresponding to each of the PGD-type compounds described following Example 16.

EXAMPLE 19

2,2-Difluoro-16-phenoxy-17,18,19,20-tetranor-PGF$_1$, bis-(tetrahydropyranyl ether).

A mixture of the reaction product of Example 10 (220 mg.), a 5 percent palladium-on-charcoal catalyst (40 mg.) and 16 ml. of diethyl acetate are stirred under hydrogen at about 0° C. until substantially all of the starting material, as shown by thin layer chromatography, is consumed. Thereafter the resulting mixture is filtered to remove catalysts and the residue is connected under reduced pressure and chromatographed yielding title product.

Following the procedure of Example 19, each of the various PGF$_2$ - or 11-deoxy-PGF$_2$ -type compound is transformed to a corresponding 11-deoxy-PGF$_1$ -or PGF$_1$ -type compound.

EXAMPLE 20 cis-4,5-Didehydro-15-methyl-17-phenyl-18,19,20-trinor-11-deoxy-PGE$_2$, methyl ester.

To a solution of the reaction product of Example 11 in dichloromethane (4 ml.) is added a solution prepared from 0.26 g. of chromium trioxide, 0.4 ml. of pyridine, and 16 ml. of dichloromethane. The mixture is then stirred for 5 min. at about 0° C. and 5 min. at about 25° C. Thereafter the resulting product is diluted with 10 ml. of ethyl acetate and filtered through silica gel. The resulting mixture is then concentrated to yield the title compound.

Following the procedure of Example 20, each of the various PGF$_a$ - or 11-deoxy-PGF -type compounds described above is transformed to the corresponding PGE- or 11-deoxy-PGE-type compound.

EXAMPLE 21 cis-4,5-Didehydro-15-methyl-17-phenyl-11-deoxy-PGF$_2$, methyl ester.

A solution of the reaction product of Example 20 in 20 ml. of methanol is cooled to −10° C. To this cooled mixture is then added sodium borohydride (80 mg.). The resulting mixture is then stirred for 40 min. at −10 to −20° C. and thereafter 2.5 ml. of an acetic acid and water (1:1) mixture is added. This mixture is then evaporated under reduced pressure and the residue shaken with ethyl acetate and water. The organic phase is then washed with aqueous sodium bicarbonate and saturated saline, dried over magnesium sulfate, and evaporated to yield crude product which is chromotographed on silica gel yielding pure title compound.

Following the procedure of Example 21, each of the various PGE- or 11-deoxy-PGE-type compounds is transformed to a corresponding PGF - or 11-deoxy-PGF -type compound.

EXAMPLE 22 cis-4,5-Didehydro-15-methyl-17-phenyl-18,19,20-trinor-11-deoxy-PGA$_2$, methyl ester A solution of the reaction product of Example 20, 4 ml. of tetrahydrofuran, and 4 ml. of 0.5N hydrochloric acid is left standing at 25° C. for 24 hr. Brine and dichloromethane in ether (1:3) are added and the mixture is stirred. The organic phase is then separated, dried, and concentrated. The residue is dissolved in diethyl ether and the resulting solution is extracted with saturated aqueous sodium bicarbonate. The aqueous phase is then acifified with dilute hydrochloric acid and then extracted with dichloromethane. This extract is then dried and concentrated to yield title product.

Following the procedure of Example 22, each of the various PGE-type compounds described following Example 20 is transformed to a corresponding PGA-type compound.

EXAMPLE 23

2-Decarboxy-2:hydroxymethyl-2,2-difluoro-16-phenoxy-17,18,19,20-tetranor-PGF$_2$ (Formula CXXII: Z$_1$ is cis-CH=CH-(CH$_2$)$_2$-CF$_2$-, Y is trans-CH=CH-, R$_7$ is phenoxy, and R$_3$ and R$_4$ of the L$_1$ moiety and R$_5$ of the M$_1$ moiety are all hydrogen).

Refer to Chart F.

A. A suspension of 2.0 g. of lithium aluminum hydride and 100 ml. of diethyl ether is prepared in a nitrogen atmosphere and thereafter a solution of 6.2 g. of 2,2-difluoro-16-phenoxy-17,18,19,20-tetranor-$PGF_{2\alpha}$, 11,15-bis-(tetrahydropyranyl ether), methyl ester in 100 ml. of diethyl ether is slowly added. The reaction mixture is then stirred for 15 min. and excess reducing agent is decomposed by careful addition of ethyl acetate and water. The precipitated inorganic material is then filtered and the residue rinsed with diethyl ether. The combined ethereal extracts are then concentrated to yield crude product.

B. The crude product described in part A is then hydrolyzed by the procedure described in Example 13.

Following the procedure of Example 23, each of the various $PGF_\alpha$ - or $PGF_\beta$ -type compounds described above is transformed to a corresponding 2-decarboxy-2-hydroxymethyl-$PGF_\alpha$ - or $PGF_\beta$ -type compound.

EXAMPLE 24

2-Decarboxy-2-hydroxyethyl-5-oxa-$PGE_2$.

Refer to Chart F.

A. Following the procedure of Example 3, Example 4, or Example 5 of the U.S. Pat. No. 3,636,120,5-oxa-$PGE_2$ (prepared according to the procedure described in Example 20 using the product of Example 14 as starting material), there is prepared respectively the oxime, methoxine, or semicarbazone of the starting material.

B. Following the procedure of Example 6, or Example 7 U.S. Pat. No. 3,636,120, the reaction product of part A of this example is transformed to a corresponding 2-decarboxy-2-hydroxymethyl-PGE-type compound.

C. Following the procedure of Example 8 or U.S. Pat. No. 3,636,120 the reaction product of part B is transformed to the title product.

Following the procedure of Example 24, but employing ethyleneketalization in place of the oxime, methoxime, or semicarbazone formation part A, and deethyleneketalization in place of the oxime, methoxime, or semicarbazone removal in part C, there is prepared the title product.

Following the procedure of Example 24, but using any of the PGE-type compounds described above, there is prepared the corresponding 2-decarboxy-2-hydroxymethyl-PGE-type compound.

Finally, following the procedure of Example 24, but using each of the various PGD, 9-deoxy-PGD, 9,10-didehydro 9-deoxy-PGD, 11-deoxy-PGE, or PGA-type compounds described above there is prepared the corresponding 2-decarboxy-2-hydroxymethyl-PG-type compound.

EXAMPLE 25

2-Decarboxy-2-hydroxymethyl-cis-4,5-didehydro-$PGF_{1\alpha}$, 2-decarboxy-2-hydroxymethyl-cis-4,5-didehydro-$PGE_1$, or 2-decarboxy-2-hydroxymethyl-cis-4,5-didehydro-$PGA_1$ (Formula CXXXV or Formula CXXXVI $Z_6$ is cis-$CH_2$-CH=CH- $(CH_2)_2$-, Y is trans-CH=CH-, $M_{18}$ is

or $$\overset{O}{\underset{\|}{}}$$

$R_3$ and $R_4$ of the $L_1$ moiety and $R_5$ of the $M_1$ moiety are all hydrogen, and $R_7$ is n-butyl).

Refer to Chart G.

A. Following the procedure of Example 10, but using the reaction product of Example 8 in place of the lactol starting material therein and employing (4-tetrahydropyranyloxybutyl)triphenylphosphonium bromide in place of 4,4-difluoro-4-carboxybutyltriphenylphosphonium bromide, there is prepared 2-decarboxy-2-tetrahydropyranyloxymethyl-cis-4,5-didehydro-$PGF_{1\alpha}$, 11,15-bis-(tetrahydropyranyl ether).

B. Following the procedure of Example 13, the reaction product of part A is hydrolyzed to the title $PGF_{1\alpha}$ -type product.

C. Following the procedure of Example 20, the reaction product of part A is transformed to the corresponding PGE-type, 11,15-bis-(tetrahydropyranyl ether). This compound is then transformed to the title $PGE_1$-type product following the procedure of Example 13.

D. Following the procedure of Example 22, the reaction product of part C is dehydrated to form the title $PGA_1$-type product.

EXAMPLE 26

2-Decarboxy-2-hydroxymethyl-15-methyl-$PGF_{2\alpha}$ or its 15-epimer

Refer to Chart F.

A. 15-Methyl-$PGF_{2\alpha}$, methyl ester (4.0 g.) is dissolved in 100 ml. of acetone, cooled to −45° C., and treated with 15 ml. of trimethylsilyldiethylamine. The reaction mixture is then stirred at −45° C. for one hr., and thereafter −10 to 0° C. for 1.5 hr. The progress of the silylation is followed by silica gel thin layer chromatography using the following solvent system: 500 ml. of ethyl acetate, 5 ml. of methanol, and 50 ml. of water are shaken and the water layer discarded. Thereafter the TLC plate is sprayed with vanallin-phosphoric acid reagent and heated. Starting material exhibits $R_f$ 0.55 and silylated product exhibits $R_f$ 0.90. The reaction mixture is then diluted with 500 ml. of diethyl ether and 100 ml. of methylene chloride and washed immediately with cold dilute sodium bicarbonate solution and saturated sodium chloride. The mixture is then dried over anhydrous magnesium sulfate. The solvent is then removed under reduced pressure at 40° C. yielding 6.22 g. of silylated product.

B. The reaction product of part A is taken up in 100 ml. of diethyl ether and added to a previously prepared suspension of 3.0 g. of lithium aluminum hydride and 100 ml. of diethyl ether. The reaction mixture is stirred for 15 min. at ambient temperature and the excess reagent decomposed by cautions addition of ethyl acetate and water. Inorganic salts are filtered from the reaction mixture and filtrate is dried and concentrated under reduced pressure at 40° C. to yield 4.8 g. $R_f =$ 0.35, employing the solvent system described in part A.

C. The trimethylsilyl protecting groups are removed by treating a methanol solution (200 ml.9 of the product of part B at 0° C. with 10 ml. of acetic acid and 100 ml. of water. The reaction mixture is stirred at ambient temperature for 15 min. and poured into 500 ml. of diethylether and 150 ml. of methylene chloride. The extract is then washed with ice cold dilute potassium bisulfate (3 g. in 100 ml. of water), cold dilute sodium bicarbonate, and brine. The resulting mixture is then dried over sodium sulfate, and evaporated under reduced pressure at 40° C., yielding 4.0 g. of crude product. This product is then purified chromatographically on 100 g. of E. Merck 7734 silica gel, partially deactivated with 40 ml. of ethyl acetate. The column is then eluted with 5 to 10 percent methanol in ethyl acetate yielding 1.29 of pure title product per 1.30 g. of crude starting material. $R_f$ is 0.50, employing the solvent system described in part A. Characteristic NMR absorptions are observed at 0.88, 1.28, 3.65, and 5.33–5.58 $\delta$. The mass spectrum of the trimethylsilyl derivative shows parent peak 642.4330 and other peaks at 627,571, 552, 537, 431, and 462.

Employing 15-epi starting material, the corresponding 15-epi product is prepared.

EXAMPLE 27

2-Decarboxy-2-hydroxymethyl-2a,2b-dihomo-15-methyl-$PGF_{2\alpha}$ or its 15-epimer Refer to Chart F.

To a stirred mixture of 0.67 g. of lithium aluminum hydride in 40 ml. of tetrahydrofuran is added 1.0 g. of 2a, 2b-dihomo-15-methyl-$PGF_{2\alpha}$, methyl ester in 30 ml. of dry tetrahydrofuran over a period of 13 min. The mixture is then stirred at ambient temperature for an additional 35 min. when the reaction is shown to be complete by thin layer chromatography. The mixture is then cooled in an ice bath while 10 ml. of ethyl acetate is added dropwise followed by the addition of 10 ml. of water dropwise. The mixture is then filtered and the filter cake washed with 75 ml. of ethyl acetate. The solvent is then evaporated from the combined filtrate and washings under reduced pressure at about 40° C. yielding an oil containing water. This material is then dissolved and the 75 ml. of ethyl acetate and dried over magnesium sulfate. Evaporation of the solvent yields 1.13 g. of an oil. This oil is chromatographed on 50 g. of silica gel eluting with 20 percent acetone and ethyl acetate. Fractions containing pure title product are combined yielding 0.84 g. of pure title product. The mass spectrum for the trimethylsilyl derivative shows parent peak at 670.4663. NMR absorptions are observed at 0.7–1.1, 1.1–2.8, 1.25, 3.48–3.8, 3.8–4.3, and 5.15–5.6 $\delta$. Infrared absorptions are observed at 3340, 3000, 2930, 2860, 1655, 1460, 1125, 1080, 1055, and 970 cm.$^{-1}$.

Following the procedures described above, but employing 1.5 g. of 15-epi-2a,2b-dihomo-15-methyl $PGF_{2\alpha}$, methyl ester there is prepared 1.21 g. of 2-decarboxy-2-hydroxymethyl-15-epi-15-methyl-$PGF_{2\alpha}$, as a pale yellow oil. The mass spectrum for the trimethylsilyl derivative shows parent peak at 670.4650 and other peaks at 655, 599, 580, 565, 509, 490, 400, 317, and 187. NMR absorptions are observed at 0.71–1.1, 1.1–2.6, 1.25, 3.58–3.8, 3.8–4.3, and 5.25–5.6 $\delta$. Infrared absorptions are observed at 3340, 3000, 2930, 2860, 1655, 1460, 1125, 1180, 1055, and 1070 cm.$^{-1}$.

EXAMPLE 28

2-Decarboxy-2-hydroxymethyl-16,16-dimethyl-$PGF_{2\alpha}$.

Refer to Chart F.

A. 16,16-Dimethyl-$PGF_{2\alpha}$, 11,15-bis-(tetrahydropyranyl ether) (2.8 g.) is dissolved in 70 ml. of diethyl ether and added dropwise to a suspension of 0.9 g. of lithium aluminum hydride in 30 ml. of diethyl ether. The reaction mixture is stirred at ambient temperature for 60 min. The excess reducing agent is decomposed by cautious addition of ethyl acetate and water, respectively. The organic salts are filtered and the filtrate is concentrated under reduced pressure to yield 2.39 g. of 2-decarboxy-2-hydroxymethyl-16,16-dimethyl-$PGF_{2\alpha}$, 11,15-bis-(tetrahydropyranyl ether). $R_f$ of this product is 0.80, employing the solvent system described in part A of Example 26. $R_f$ of the starting material is 0.45 employing the same system.

B. The reaction product of part A (1.0 g.) is taken up in 15 ml. of acetic acid, 7 ml. of water and 2 ml. of tetrahydrofuran. This mixture is then warmed to 40° C. for 5 hr. The resulting product is then diluted with 15 ml. of water and frozen in a dry-ice acetone bath and lopholyzed. Crude product is then chromatographed over 100 g. of E. Merck 7734 silica gel, partially deactivated with 40 ml. of ethyl acetate and wetted with ethyl acetate. The column is then eluted with 0–10 percent methanol in ethyl acetate, yielding 438 mg. of pure title product. Characteristics NMR absorptions are observed at 0.85, 0.90, and 5.25–5.67$\delta$. The mass spectrum of the trimethylsilyl derivative shows peaks at 656, 641, 566, 557, 467, and 441.

EXAMPLE 29

2-Decarboxy-2-hydroxymethyl-15-methyl-$PGE_2$

Refer to Chart F.

A. 2-Decarboxy-2-hydroxymethyl-15-methyl-$PGF_2$ (2.55 g.) is dissolved in 100 ml. of acetone and treated with 15 ml. of trimethylsilyldiethylamine at −45 to −40° C. for 4 hr. Silylated reaction product is then recovered by the procedure described in Example 26, part A.

B. The residue obtained in part A above is treated at 15° C. for 15 min. with the Collins reagent. This reagent is prepared from 4.25 g. of chromium oxide, 6.9 ml. of pyridine, and 150 ml. of methylene chloride stirred at 15°–20° C. for 45 min. The reaction mixture is then filtered through a pad of equal parts Celite filteraid and E. Merck 7734 silica gel. The resulting mixture is then concentrated under reduced pressure and the residue taken up in benzene and filtered as described above to remove chromium salt.

C. The filtrate obtained in part B is then reconcentrated to afford 2.6 g. of crude silylated product which is dissolved in 100 ml. of water and treated at 0° C. for 15 min. with 5 ml. of acetic acid and 50 ml. of water to hydrolyze the silyl groups. This reaction mixture is then poured into 400 ml. of diethyl ether and 100 ml. of methylene chloride and washed with cold dilute sodium bicarbonate and saturated saline before drying over sodium sulfate. The extract obtained in then concentrated to yield 1.6 g. of crude product which is chromatographed over 160 g. of E. Merck 7734 silica gel partially deactivated with 65 ml. of ethyl acetate and wetted with 80 percent ethyl acetate in hexane. The column is then eluted with 80 percent ethyl acetate in hexane, ethyl acetate, and 5 percent methanol in ethyl acetate, respectively. Accordingly, there is obtained 220 mg. of pure title product. Characteristic NMR absorptions are observed at 0.88, 1.30, 3.23–3.72, and 5.26–5.67 $\delta$. Characteristic infrared absorptions are observed at 1750 and 3400 cm.$^{-1}$. The mass spectrum shows parent peak at 568.3794 and other peaks at 553, 497, 478, 463, 407, and 388 for the trimethylsilyl derivative.

Following the procedure of the above Examples each of the 2-decarboxy-2-hydroxymethyl-PGF$_\alpha$ compounds described in the Table(s) below is prepared.

Further, following the procedure of the above Examples each of the various 11-deoxy-PGF$_\alpha$ -, PGE-, 11-deoxy-PGE-, PGF$_\beta$ -, 11-deoxy-PGF$_\beta$ -, PGD-, 9-deoxy-PGD-, or 9-deoxy-9,10-didehydro-PGD-type compounds corresponding to each of the PGF$_\alpha$ -type compounds described in the Table(s) is prepared.

Table A

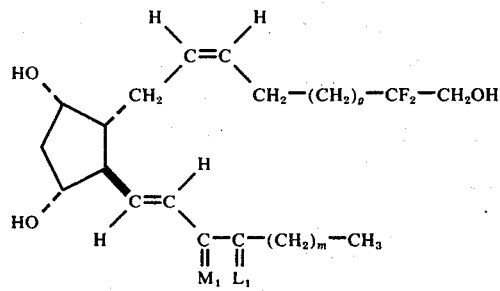

2,2-Difluoro-2-decarboxy-2-hydroxymethyl-PGF$_{2\alpha}$-type compounds

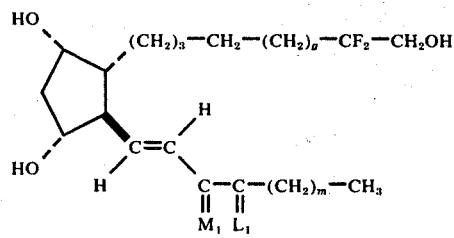

2,2-difluoro-2-decarboxy-2-hydroxymethyl-PGF$_{1\alpha}$-type compounds

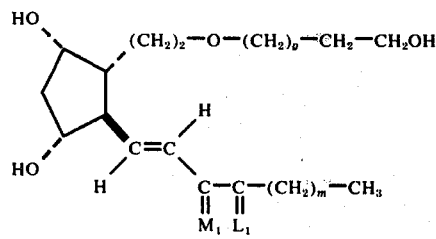

5-oxa-2-decarboxy-2-hydroxymethyl-PGF$_{1\alpha}$-type compounds

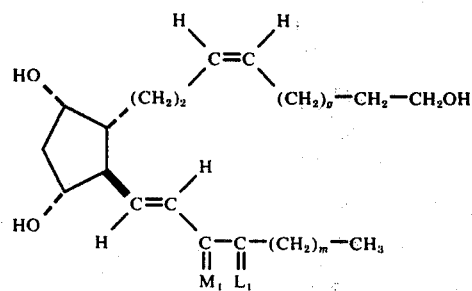

cis-4,5-didehydro-2-decarboxy-2-hydroxymethyl-PGF$_{1\alpha}$-type compounds

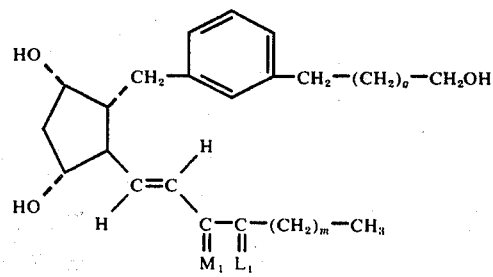

3,7-inter-m-phenylene-4,5,6-trinor-2-decarboxy-2-hydroxymethyl-PGF$_{1\alpha}$-type compounds Table A-continued

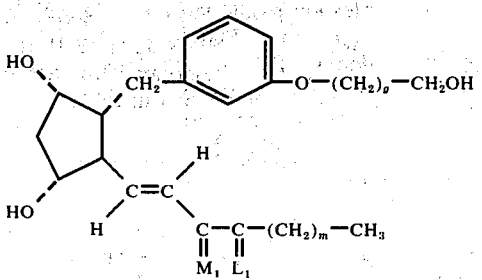

3,7-inter-m-phenylene-4,5,6-trinor-3-oxa-2-decarboxy-2-hydroxymethyl-PGF$_{1\alpha}$-type compounds

| Example | g | m | L$_1$ R$_3$ | R$_4$ | M$_1$ R$_5$ | ~OH | Name |
|---|---|---|---|---|---|---|---|
| A-1 | 1 | 3 | methyl | hydrogen | hydrogen | α | 16-methyl |
| A-2 | 1 | 3 | methyl | hydrogen | methyl | α | 15,16-dimethyl |
| A-3 | 1 | 3 | methyl | methyl | hydrogen | α | 16,16-dimethyl |
| A-4 | 1 | 3 | methyl | methyl | methyl | α | 15,16,16-trimethyl |
| A-5 | 1 | 3 | fluoro | hydrogen | hydrogen | α | 16-fluoro |
| A-6 | 1 | 3 | fluoro | hydrogen | methyl | α | 15-methyl-16-fluoro |
| A-7 | 1 | 3 | fluoro | fluoro | hydrogen | α | 16,16-difluoro |
| A-8 | 1 | 3 | fluoro | fluoro | methyl | α | 15-methyl-16,16-difluoro |
| A-9 | 1 | 3 | hydrogen | hydrogen | hydrogen | α | (title compound) |
| A-10 | 3 | 3 | hydrogen | hydrogen | hydrogen | α | 2a,2b-dihomo |
| A-11 | 3 | 3 | methyl | methyl | hydrogen | α | 2a,2b-16,16-dimethyl |
| A-12 | 3 | 3 | methyl | methyl | methyl | α | 2a,2b-dihomo-15,16,16-trimethyl |
| A-13 | 3 | 3 | fluoro | fluoro | hydrogen | α | 2a,2b-dihomo-16,16-difluoro |
| A-14 | 3 | 3 | fluoro | fluoro | methyl | α | 2a,2b-dihomo-15-methyl-16,16-difluoro |

I claim:
1. A prostaglandin analog of the formula

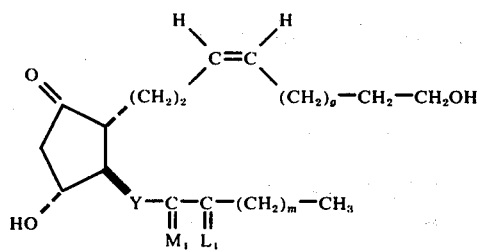

wherein Y is trans-CH=CH-;
wherein M$_1$ is

or

wherein R$_5$ is hydrogen or methyl;
wherein L$_1$ is

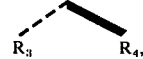

or a mixture of

and

wherein R$_3$ and R$_4$ are hydrogen, methyl, or fluoro, the same or different, with the proviso that one of R$_3$ and R$_4$ is methyl only when the other is hydrogen or methyl;
wherein g is one, 2, or 3; and
wherein m is one to 5, inclusive.

2. A compound according to claim 1, wherein m is one or 2.

3. A compound according to claim 1, wherein m is 4 or 5.

4. A compound according to claim 1, wherein m is 3.

5. A compound according to claim 4, wherein g is one.

6. A compound according to claim 5, wherein at least one of R$_3$ and R$_4$ is fluoro.

7. A compound according to claim 6, wherein R$_3$ and R$_4$ are both fluoro.

8. A compound according to claim 7, wherein R$_5$ is hydrogen.

9. 2-Decarboxy-2-hydroxymethyl-cis-4,5-didehydro-16,16-difluoro-PGE$_1$, a compound according to claim 8.

10. 2-Decarboxy-2-hydroxymethyl-cis-4,5-didehydro-16,16-difluoro-15-epi-PGE$_1$, a compound according to claim 8.

11. A compound according to claim 5, wherein at least one of R$_3$ and R$_4$ is methyl.

12. A compound according to claim 11, wherein R$_3$ and R$_4$ are both methyl.

13. A compound according to claim 12, wherein R$_5$ is hydrogen.

14. 2-Decarboxy-2-hydroxymethyl-cis-4,5-didehydro-16,16-dimethyl-PGE$_1$, a compound according to claim 13.

15. 2-Decarboxy-2-hydroxymethyl-cis-4,5-didehydro-16,16-dimethyl-15-epi-PGE$_1$, a compound according to claim 13.

16. A compound according to claim 5, wherein R$_3$ and R$_4$ are both hydrogen.

17. A compound according to claim 16, wherein R$_5$ is methyl.

18. 2-Decarboxy-2-hydroxymethyl-cis-4,5-didehydro-15-methyl-PGE$_1$, a compound according to claim 17.

19. 2-Decarboxy-2-hydroxymethyl-cis-4,5-didehydro-15-epi-15-methyl-PGE$_1$, a compound according to claim 17.

20. A compound according to claim 16, wherein R$_5$ is hydrogen.

21. 2-Decarboxy-2-hydroxymethyl-cis-4,5-didehydro-PGE$_1$, a compound according to claim 20.

22. 2-Decarboxy-2-hydroxymethyl-cis-4,5-didehydro-15-epi-PGE$_1$, a compound according to claim 20.

* * * * *

Page One of 7

UNITED STATES PATENT OFFICE
CERTIFICATE OF CORRECTION

Patent No. 4,028,419    Dated June 7, 1977

Inventor(s) Norman A. Nelson

It is certified that error appears in the above-identified patent and that said Letters Patent are hereby corrected as shown below:

Column 1, lines 28-31, that portion of the formula reading:

should read 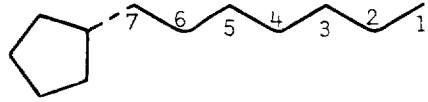

Column 2, line 35, "attachement" should read -- attachment --; line 53, "tissures" should read -- tissues --;
Column 6, line 42, "protaglandins" should read -- prostaglandins --;
Column 7, line 1, "perserved" should read -- preserved --; line 49, "pregnant an" should read -- pregnant and --;
Column 10, lines 10-15, that portion of the formula reading

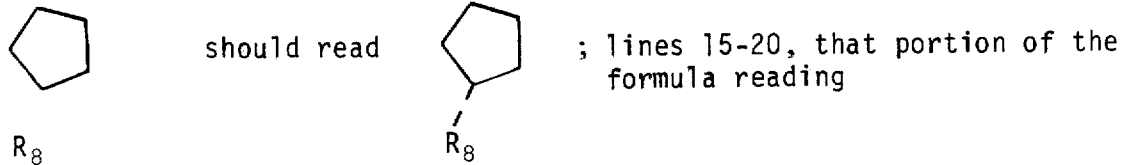; lines 15-20, that portion of the formula reading

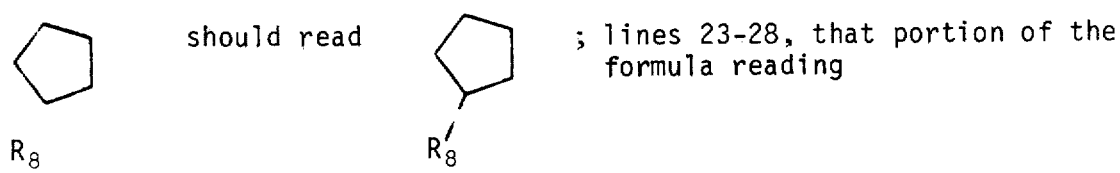; lines 23-28, that portion of the formula reading

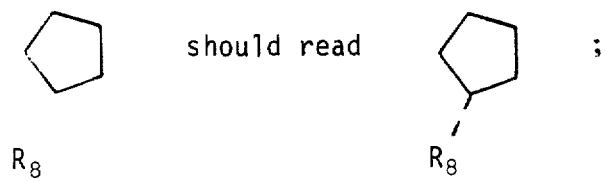;

UNITED STATES PATENT OFFICE
CERTIFICATE OF CORRECTION

Patent No. 4,028,419    Dated  June 7, 1977

Inventor(s)  Norman A. Nelson

It is certified that error appears in the above-identified patent and that said Letters Patent are hereby corrected as shown below:

Column 10, lines 30-35, that portion of the formula reading

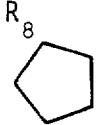         should read         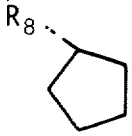

Column 12, line 66, "$-(CH_2)_g-CH_2-$," should read -- $-(CH_2)_g-CF_2-$ -- ;

Column 15, line 10, "PGF-type" should read -- PGFα-type --; line 61, "PGF-" should read -- PGFα- --;

Column 16, line 13, "cis-Ch=" should read -- cis-CH= --;  line 19, "contains1" should read -- contains --;

Column 17, line 63, "p-trifluoromethyl)-" should read -- p-(trifluoromethyl)- --;

Column 18, line 13, "-PFGα-" should read ---PGFα- -- ; line 24, "PFGα" should read -- PGFα --;

Columns 27-28, lines 57-65, that portion of formula XL reading

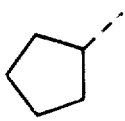                    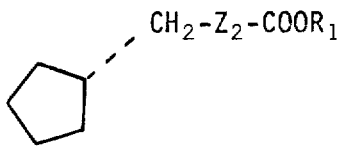

Column 30, line 33, that portion of the formula reading

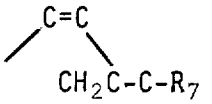         should read         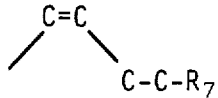

UNITED STATES PATENT OFFICE
CERTIFICATE OF CORRECTION

Patent No. 4,028,419          Dated June 7, 1977

Inventor(s) Norman A. Nelson

It is certified that error appears in the above-identified patent and that said Letters Patent are hereby corrected as shown below:

Column 31, lines 25-30, that portion of formula LXXX reading

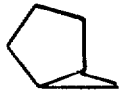      should read      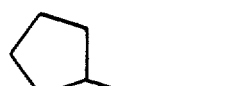 ;

Column 32, lines 5-10, that portion of formula XCI reading

      should read       ;

Column 35, lines 15-20, that portion of formula CXXXI reading

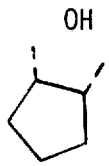      should read      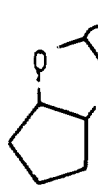 ;

Column 35, lines 35-43, that portion of formula CXXXIII reading

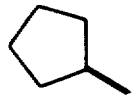      should read      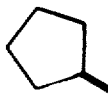 ;

UNITED STATES PATENT OFFICE
CERTIFICATE OF CORRECTION

Patent No. 4,028,419      Dated June 7, 1977

Inventor(s) Norman A. Nelson

It is certified that error appears in the above-identified patent and that said Letters Patent are hereby corrected as shown below:

Column 38, line 34: "1methyl-3-phenylpropyl," should read -- 1-methyl-3-phenylpropyl, --;
Column 39, line 34, "4-)-netrobenzoyl," should read -- 4-)-nitrobenzoyl,
Column 46, lines 3 and 6, "( -carboxyalkyl)" should read -- ($\omega$-carboxyalkyl) --; line 13, "$PGF_1$-, 11-deoxy-$PGF_2$-" should read -- $PGF_1\alpha$-, 11-deoxy-$PGF_2\alpha$- --,; line 14, "$PGF_1$- or $PGF_2$-" should read -- $PGF_1\alpha$-, or $PGF_2\alpha$- --; line 27, "$PGF_1$ -type" should read -- $PGF_1\alpha$-type --;
Column 47, line 14, "PGF-" should read -- $PGF\beta$- --;
Column 48, line 16, "$PGF_1$ -or" should read -- $PGF_1\alpha$- or --; line 16, "$PGF_1$-type" should read -- $PGF_1\alpha$-type --;

Column 50, line 7, "i.e. $R_{63}$" should read -- i.e. $R_{64}$ --; line 8, "($R_{64}$C-) hd 20," should read -($R_{64}$C-)$_2$O,- ; line 18, "(2 to 3)-" should read -- (2 or 3) --; line 28, "-6nitro-" should read -- -6-nitro- --;
Column 51, line 56, "chlorotrim-" should read -- chlorotri-m- --;
Column 53, line 45, "friction" should read -- fraction --;
Column 55, line 3, "formula la" should read -- formula --; line 30, "LXXI to LXXIV" should read -- LXXXI to LXXXIV --;
Column 56, line 10, "PGF -type" should read -- $PGF\alpha$-type --;
Column 58, line 64, "PGF -type" should read -- $PGF\beta$-type --
Column 59, line 17, "( -tetrahy-" should read -- ($\omega$-tetrahy- --; line 19, "( -carboxyalkyl)" should read -- ($\omega$-carboxyalkyl) --; line 22, "( -hydroxymethylalkyl)" should read -- ($\omega$-hydroxymethylalkyl) --; line 54, "PGF-" should read -- $PGF\alpha$- --;
Column 69, line 14, "$PGF_1$," should read -- $PGF_1\alpha$, --; line 48, "$PGF_1$-type" should read -- $PGF_1\alpha$-type --; line 60, "$PGF_1$ or 11-deoxy-$PGF_1$-" should read -- $PGF_1\alpha$ or 11-deoxy-$PGF_1\alpha$- --; line 63, $PGF_2$-" should read -- $PGF_2\alpha$- --; line 64, "$PGF_2$-type" should read -- $PGF_2\alpha$-type --;
Column 70, line 1, "$PGF_2$-type" should -- $PGF_2\alpha$-type --; line 6, "$PGF_2$," should read -- $PGF_2\alpha$, --; line 7, "(Formula XXXII:" should read -- (Formula XXXIII --; line 38, "$PGF_2$," should read -- $PGF_2\alpha$, --;

UNITED STATES PATENT OFFICE
CERTIFICATE OF CORRECTION

Patent No. 4,028,419　　　　　　　　Dated June 7, 1977

Inventor(s) Norman A. Nelson

It is certified that error appears in the above-identified patent and that said Letters Patent are hereby corrected as shown below:

Column 70, line 50, "15-epiPGF$_2$," should read -- 15-epi PGF$_2\alpha$, --; line 57, "PGF$_2$-type" should read -- PGF$_2\alpha$-type --; line 62, "PGF$_1$," should read -- PGF$_1\alpha$, --;

Column 71, line 37, "PGF$_1$ ." should read -- PGF$_1\alpha$. --; lines 62 and 64, "PFG$_2$" should read -- PGF$_2\alpha$ --;

Column 72, line 7, "PFG$_1$ ," should read -- PGF$_1\alpha$, --; lines 28, 55, 59, "PGF$_1$" should read -- PGF$_1\alpha$ --;

Column 73, line 34, ":CH$_2$-C(CH$_3$)$_2$-CH$_2$-" should read -- -CH$_2$-C(CH$_3$)$_2$-CH$_2$- --; line 51, "(C=0.8967" should read -- (C=0.8976 --;

Column 75, line 43, "nbutyllithium" should read -- n-butyllithium --;

Column 76, line 4, "m-[(carboxy)methoxy]-benzyl -" should read -- {m-[(carboxy)methoxy]-benzyl}- --; line 25, "PGF$_1$" should read -- PGF$_1\alpha$ --;

Column 77, line 44, "PGF$_1$" should read -- PGF$_1\alpha$ --; line 57, "PGF$_1$-type" should read -- PGF$_1\alpha$-type --; line 62, "PGF$_2$," should read -- PGF$_2\alpha$, --;

Column 78, line 21, "PGF$_2$," should read -- PGF$_2\alpha$, --; line 23, "PGF$_2$," should read -- PGF$_2\alpha$, --; line 49, "PGF -type" should read -- PGF$\alpha$-type --;

Column 79, line 53, "PGF$_1$," should read -- PGF$_1\alpha$, --; line 66, "PGF$_2$- or 11-deoxy-PGF$_2$-" should read -- PGF$_2\alpha$- or 11-deoxy-PGF$_2\alpha$- --; line 68, "PGF$_1$- or PGF$_1$-type" should read -- PGF$_1\alpha$- or PGF$_1\alpha$-type --;

Column 80, line 22, "PGF$_2$," should read -- PGF$_2\beta$, --; lines 37 and 38, "PGF -" should read -- PGF$\beta$- --; line 52, "acifified" should read -- acidified --; line 62, "PGF$_2$" should read -- PGF$_2\alpha$ --; line 16, "11-deoxy-PGF -type" should read -- 11-deoxy-PGF$\alpha$-type --;

UNITED STATES PATENT OFFICE
CERTIFICATE OF CORRECTION

Patent No. 4,028,419            Dated June 7, 1977

Inventor(s)   Norman A. Nelson

It is certified that error appears in the above-identified patent and that said Letters Patent are hereby corrected as shown below:

Column 82, line 64, "200 ml. 9" should read -- (200 ml.) --;
Column 84, line 33, "PGF2" should read --$PGF_{2\alpha}$ --;

UNITED STATES PATENT AND TRADEMARK OFFICE
CERTIFICATE OF CORRECTION

PATENT NO. : 4,028,419
DATED : June 7, 1977
INVENTOR(S) : Norman A. Nelson

It is certified that error appears in the above-identified patent and that said Letters Patent are hereby corrected as shown below:

Column 11, line 22, should read -- $-CH_2-O-CH_2-(CH_2)_g-CH_2-,$ --

Column 16, line 32, should read -- $-CH_2-O-CH_2-(CH_2)_g-CH_2-$ --

Columns 85-86, approximately line 37, in the side chain, should read -- $(CH_2)_2-O-CH_2-(CH_2)g-CH_2-CH_2OH$ --

Signed and Sealed this

Sixth Day of June 1978

[SEAL]

Attest:

RUTH C. MASON
*Attesting Officer*

DONALD W. BANNER
*Commissioner of Patents and Trademarks*